(12) United States Patent
Dong

(10) Patent No.: US 6,900,010 B2
(45) Date of Patent: May 31, 2005

(54) COMPOSITIONS AND METHODS FOR DETECTING HUMAN IMMUNODEFICIENCY VIRUS

(75) Inventor: Jian-Yun Dong, Mt. Pleasant, SC (US)

(73) Assignee: MUSC Foundation For Research Development, Charleston, SC (US)

( * ) Notice: Subject to any disclaimer, the term of this patent is extended or adjusted under 35 U.S.C. 154(b) by 130 days.

(21) Appl. No.: 10/244,140

(22) Filed: Sep. 13, 2002

(65) Prior Publication Data

US 2003/0064054 A1 Apr. 3, 2003

Related U.S. Application Data

(63) Continuation-in-part of application No. 10/112,579, filed on Mar. 29, 2002, which is a division of application No. 09/559,244, filed on Apr. 26, 2000, now Pat. No. 6,410,013, which is a continuation-in-part of application No. 09/314,259, filed on May 18, 1999, now Pat. No. 6,406,911.

(60) Provisional application No. 60/117,136, filed on Jan. 25, 1999.

(51) Int. Cl.[7] .................................................. C12Q 1/70
(52) U.S. Cl. ...................... 435/5; 424/93.2; 424/93.6; 424/208.1; 424/233.1; 435/6; 435/8; 435/14; 435/69.1; 435/70.1; 435/172.3; 435/207; 435/235; 435/240.2; 435/320.1; 435/325; 435/372.3; 435/455; 514/44; 536/22.1; 536/23.4; 536/23.72; 536/24.1
(58) Field of Search .......................... 435/5, 8, 6, 69.1, 435/14, 34, 70.1, 172.3, 207, 235.1, 240.2, 325, 320.1, 372.3, 455; 536/22.1, 23.4, 23.72, 24.1; 424/93.2, 93.6, 208.1, 233.1; 514/44

(56) References Cited

FOREIGN PATENT DOCUMENTS

| GB | 2 244 712 A | 12/1991 |
| WO | WO 93/05185 | 3/1993 |
| WO | WO 00/43515 | 7/2000 |

OTHER PUBLICATIONS

Jamieson, B.D. et al., "In Vivo Pathogenesis of a Human Immunodeficiency Virus Type 1 Reporter Virus", Journal of Virology, Aug. 1998, vol. 72, No. 8, pp. 6520–6526.

Dorsky, D.I. et al., "Detection of HIV–1 Infection With a Green Fluorescent Protein Reporter System", Journal of Immune Deficiency Syndromes, vol. 13, No. 4, 1996.

Lee, A.H. et al., "Generation of the Replication–Competent Human Immunodeficiency Virus Type 1 Which Expresses A Jellyfish Green Fluorescent Protein", Biochemical and Biophysical Research Communications, vol. 233, pp. 288–292, 1997.

Koseki, S. et al., A Simple Assay System For Examination of the Inhibitory Potential In Vivo of Decoy RNA's, Ribozymes and other Drugs By Measuring the Tat–Mediated Transcription of a Fusion Gene Composed of the Long Terminal Repeat of HIV–1 and a Gene For Luciferase.

Gervaix, A. et al., "A New Reporter Cell Line To Monitor HIV Infection and Drug Susceptibility In Vitro", Proc. Natl. Acad. Sci USA, vol. 94, pp. 4653–4658, Apr. 1997.

Pirounaki, Maria et al., "Rapid Phenotypic Drug Susceptibility Assay For HIV–1 With a CCR5 Expressing Indicator Cell Line", Journal of Virological Methods 85 (2000), Ppages 151–161.

Mattias J. Schnell et al., Construction of a Novel Virus That Targets HIV–1–Infected Cells and Controls HIV–1 Infection, Cell, Sep. 5, 1997, vol. 90, pp. 849–857.

Yi–Fu Yang et al., IL–12 as well as IL–2 Upregulates CCR5 Expression on T Cell Receptor–Triggered Human CD4+ T Cells, Journal of Clinical Immunology, vol. 21, No. 2, pp. 116–125.

*Primary Examiner*—Ulrike Winkler
(74) *Attorney, Agent, or Firm*—Benjamin Aaron Adler

(57) ABSTRACT

Methods are provided for screening natural and synthetic anti-HIV agents using recombinant cells that are rendered susceptible to productive infection of various strains, subtypes or clades of HIV from both laboratory and clinical isolates. The method comprises: taking a culture of recombinant cells in which at least one of the recombinant cells comprises a reporter sequence comprising a reporter gene whose expression is regulated by a protein specific to HIV, and a heterologous sequence which encodes CD4 and one or more additional cell surface receptors, wherein the heterologous sequence expresses CD4 and the one or more additional cell surface receptors at elevated levels as compared to the cell in the absence of expression by the heterologous sequence such that productive infection of the recombinant cell by HIV is achieved, which is defined by HIV viral replication and the infection of non-infected cells in the culture of the recombinant cells; contacting the cell culture with a sample containing HIV; adding a tester agent to the cell culture; and detecting a change in a level of expression of the reporter gene in the cells in the culture.

67 Claims, 15 Drawing Sheets

FIGURE 8
A.
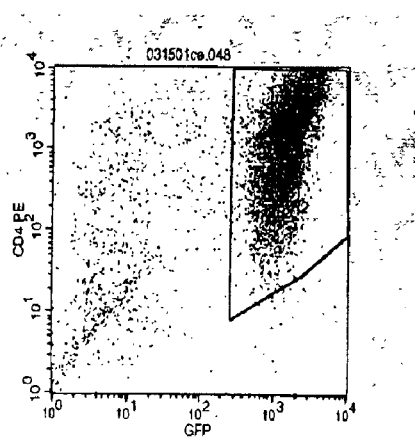
CD4 Expression Level: 84.0 %
B.
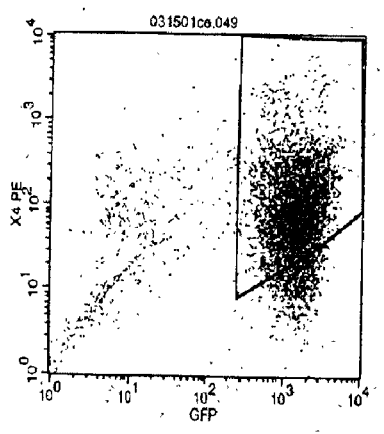
CXCR4 Expression Level: 77.7 %
C.
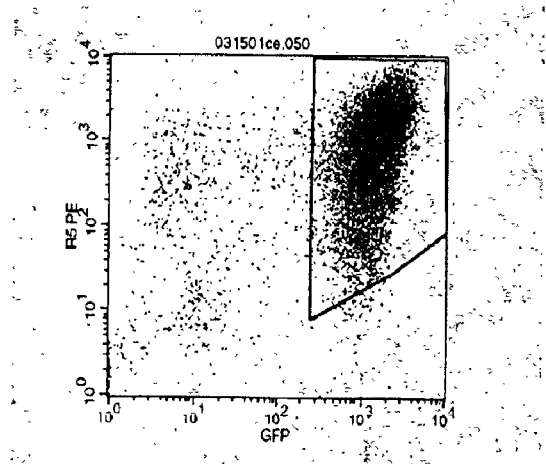
CCR5 Expression Level: 89.6 %

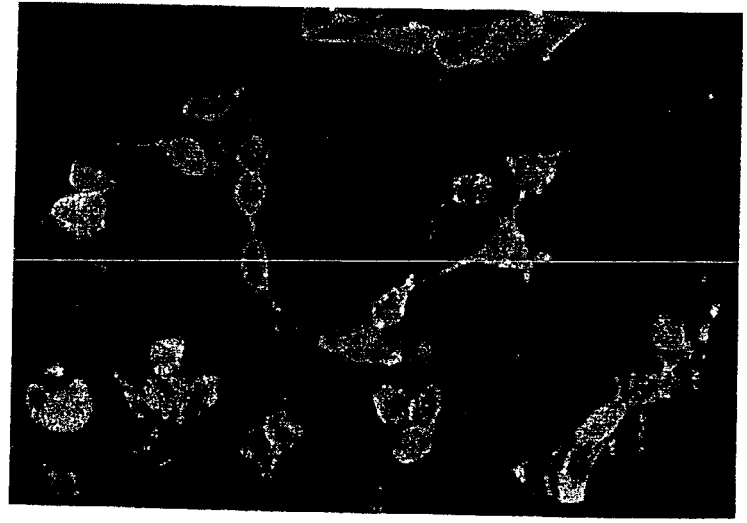
FIGURE 8

FIGURE 8G

| # | Cell Types | Infected | Fluorescent-PE Ab | All %Gated | M1 %Gated | All Mean | M1 Mean | All Geo Mean | M1 Geo Mean |
|---|---|---|---|---|---|---|---|---|---|
| 1 | HUT78 | non | mouse IgG 2aκ-PE | 100 | 1.2 | 4.04 | 21.74 | 3.35 | 18.83 |
| 2 | | non | CD4-PE | 100 | 99.92 | 628.77 | 629.25 | 484.56 | 486.22 |
| 3 | | non | CXCR4-PE | 100 | 65.29 | 24.21 | 32.1 | 18.27 | 26.74 |
| 4 | | non | CCR5-PE | 100 | 1.56 | 4.14 | 27.48 | 3.34 | 23.44 |
| 5 | CEM-NKr-R5 | non | mouse IgG 2aκ-PE | | | | | | |
| 6 | | non | CD4-PE | 100 | 3.12 | 3.74 | 19.8 | 3.05 | 16.24 |
| 7 | | non | CXCR4-PE | 100 | 99.6 | 343.3 | 344.67 | 285.47 | 290.65 |
| 8 | | non | CCR5-PE | 100 | 98.99 | 65.93 | 66.55 | 53.8 | 55.13 |
| | | | | 100 | 66.66 | 38.76 | 55.64 | 16.91 | 32.66 |
| 9 | Molt-4-R5 | non | mouse IgG 2aκ-PE | 100 | 1.15 | 3.87 | 31.78 | 3.31 | 20.82 |
| 10 | | non | CD4-PE | 100 | 57.1 | 35.1 | 57.41 | 15.58 | 39.05 |
| 11 | | non | CXCR4-PE | 100 | 91.44 | 73.1 | 79.25 | 47.6 | 57.08 |
| 12 | | non | CCR5-PE | 100 | 59.66 | 37.1 | 57.94 | 17.75 | 38.66 |
| 13 | CEM-A | non | mouse IgG 2aκ-PE | 100 | 0.59 | 3.38 | 14.07 | 3.01 | 12.31 |
| 14 | | non | CD4-PE | 100 | 94.44 | 98.93 | 104.5 | 62.23 | 73.75 |
| 15 | | non | CXCR4-PE | 100 | 99.69 | 87.06 | 87.31 | 69.86 | 70.36 |
| 16 | | non | CCR5-PE | 100 | 0.24 | 3.06 | 33.62 | 2.7 | 17.45 |
| 17 | MEGI | non | mouse IgG 2aκ-PE | 100 | 2.1 | 6.17 | 19.43 | 5.45 | 18.61 |
| 18 | | | CD4-PE | 100 | 96.7 | 126.69 | 130.76 | 97.19 | 106.47 |
| 19 | | | CXCR4-PE | 100 | 50.34 | 16.25 | 22.6 | 14.18 | 21.27 |
| 20 | | | CCR5-PE | 100 | 2.03 | 6.34 | 20.31 | 5.62 | 19.43 |
| 21 | Indicator#44 | 3R122900 | mouse IgG 2aκ-PE | 100 | 1.86 | 4.96 | 27.72 | 4.16 | 19.95 |
| 22 | | MOI, 30 | CD4-PE | 100 | 95.19 | 577.67 | 584.4 | 271.07 | 324.48 |
| 23 | | | CXCR4-PE | 100 | 95.78 | 177.72 | 185.15 | 108.28 | 121.08 |
| 24 | | | CCR5-PE | 100 | 92.42 | 258.22 | 278.69 | 132.99 | 167.66 |
| 25 | Indicator#44 | 3R122900 | mouse IgG 2aκ-PE | 100 | 2.08 | 5.11 | 32.83 | 4.21 | 23.34 |
| 26 | | MOI, 60 | CD4-PE | 100 | 93.42 | 894.83 | 957.23 | 393.37 | 518.33 |
| 27 | | | CXCR4-PE | 100 | 93.88 | 219.61 | 233.8 | 125.85 | 150.97 |
| 28 | | | CCR5-PE | 100 | 91.64 | 369.08 | 401.96 | 175.48 | 232.68 |

FIGURE 9
A.
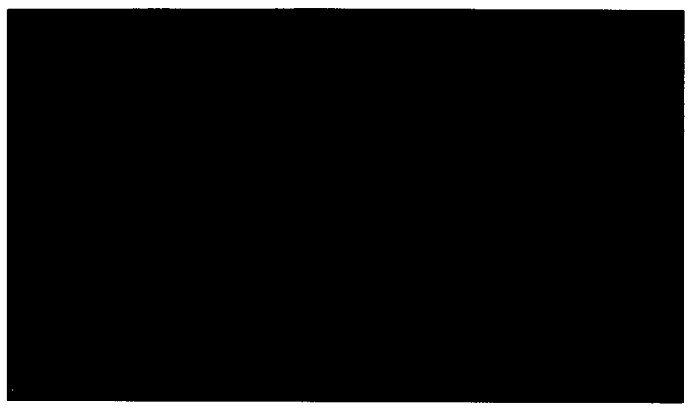
B.
C.
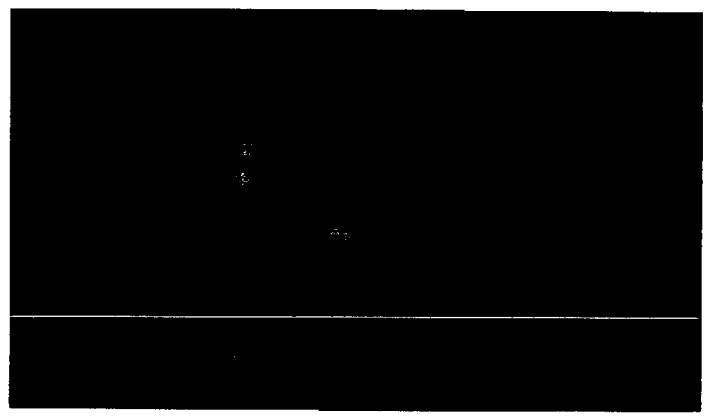

FIGURE 10

Table 1. Viral infection of Indicator Cells by HIV-1 Subtypes

| Cat. No. | Inhibition by IIIB Ab (4 µl) | Subtype (gag/env) | Viral Titer (ip/ml) | Co-receptor | NIH p24 (ng/ml) | Phenotype |
|---|---|---|---|---|---|---|
| 398 | (HTLV-IIIB/H9) 100% (50 ip) 88% (225 ip) 83% (400 ip) | B/B | $2.0 \times 10^5$ | X4 | | SI (+++) |
| 1650 | (92UG029) 16% (170 ip) 35% (600 ip) | A/A | $8.9 \times 10^3$ | X4 | 47 | SI (+) |
| 1996 | (93RW002) | /A | $1.9 \times 10^2$ | R5 | 121 | SI |
| 2304 | (94UG103) 29% (37 ip) 12% (185 ip) | /A | $3.7 \times 10^3$ | R5,X4 | 155 | SI (++) |
| 1658 | (92TH014) | B/B | $1.2 \times 10^4$ | R5 | 177 | SI |
| 2308 | (93BR012) 16% (120ip) 38% (660 ip) | /B | $1.2 \times 10^4$ | R5 | 316 | SI (+) |
| 1777 | (92BR025) 8% (120 ip) 10% (500 ip) | C/C | $1.0 \times 10^4$ | R5 | 164 | NSI*(±) |
| 4164 | (98CN006) | C/C | $8.8 \times 10^3$ | R5 | 160 | SI |
| 1684 | (92UG005) 23% (400 ip) 22 % (1200 ip) | D/D | $1.7 \times 10^4$ | R5 | 225 | SI (+) |
| 1952 | (93UG065) | D/D | $1.6 \times 10^3$ | X4 | 245 | SI |
| 2166 | (93TH053) | /E | $1.4 \times 10^3$ | X4 | 45 | NSI* |
| 2167 | (93TH054) | /E | $2.4 \times 10^3$ | R5 | 58 | SI |
| 2314 | (93BR019) 40% (86 ip) 23% (430 ip) | /BF | $8.6 \times 10^3$ | X4 | 128 | SI (++) |
| 2329 | (93BR020) | F/F | $5.7 \times 10^3$ | R5, X4 | 169 | SI |
| 2338 | (93BR029) 33% (300 ip) | B/F | $5.8 \times 10^3$ | R5 | 185 | SI (+++) |
| 4143 | (BCF13) 32% (180 ip) | Group O | $2.9 \times 10^4$ | | | SI (+++) |

All viruses were titered between day 3 and day 4 postinfection
* At day 4, there were no syncytial formed.

FIGURE 11

| Comparison GenPhar Indicator with MAGI Cells | | | | | | | |
|---|---|---|---|---|---|---|---|
| HIV | HIV Strains | Sources | Catalogue | Co-Receptor | Indicator#44 (ip/ml) | MEGI (ip/ml) | Indicator/MEGI |
| Wild type | IIIB | NIH | 398 | X4 | 75,000 | 66,000 | 1.14 |
| Patient's Isolates | JM | GenPhar, INC | | X4 | 1,050 | 490 | 2.14 |
| Patient's Isolates | 92UG001 | NIH | 1647 | X4, R5 | 5,200 | 1,900 | 2.74 |
| Patient's Isolates | 93TH054 | NIH | 2167 | R5 | 4,800 | 0 | 0.00 |
| Patient's Isolates | 93BR020 | NIH | 2329 | X4R5 | 5,250 | 530 | 9.91 |

COMPOSITIONS AND METHODS FOR DETECTING HUMAN IMMUNODEFICIENCY VIRUS

CROSS REFERENCE TO RELATED APPLICATIONS

This application is a continuation-in-part of application entitled "METHODS OF MONITORING HIV DRUG RESISTANCE USING ADENOVIRAL VECTORS", Ser. No. 10/112,579, filed on Mar. 29, 2002, which is a divisional of application entitled "VIRAL VECTORS FOR USE IN MONITORING HIV DRUG RESISTANCE," Ser. No. 09/559,244, filed on Apr. 26, 2000, now U.S. Pat. No. 6,410,013, which is continuation-in-part of application entitled "METHODS OF MONITORING HIV DRUG RESISTANCE," Ser. No. 09/314,259, filed on May 18, 1999, now U.S. Pat. No. 6,406,911, which claims priority to provisional application entitled "METHODS OF MONITORING HIV DRUG RESISTANCE," Ser. No. 60/117,136, filed on Jan. 25, 1999. The above applications are incorporated herein by reference.

BACKGROUND OF THE INVENTION

1. Field of the Invention

The present invention relates to recombinant vectors and cell lines, and methods for detecting and monitoring viral infection. More particularly, the invention relates to recombinant vectors and cell lines, and methods for detecting HIV infection, monitoring HIV for drug resistance and screening for anti-HIV agents.

2. Description of Related Art

Human immunodeficiency virus (HIV) has been implicated as the primary cause of the slowly degenerate disease of the immune system termed acquired immune deficiency syndrome (AIDS). Infection of the $CD4^+$ subclass of T-lymphocytes with the HIV type-1 virus (HIV-1) leads to depletion of this essential lymphocyte subclass which inevitably leads to opportunistic infections, neurological disease, neoplastic growth and eventual death.

Infection with human immunodeficiency virus (HIV) is a chronic process with persistent, high rates of viral replication. The pathogenesis of HIV-1 infection is characterized by a variable but often prolonged asymptomic period following the acute viremic phase. Previous work has established a correlation between HIV disease progression and increasing amounts of infectious virus, viral antigens, and virus-specific nucleic acids (Ho et al., New England. J. Med. 321: 1621–1625 (1989); Schnittman et al. AIDS Res. Hum. Retroviruses 7: 361–367 (1991); Pantalco et al. Nature 362: 355–358 (1993)).

A variety of reagents and assays have been developed to detect the infection of HIV and monitor the progression of HIV in the body. For example, counting the depletion of CD4+ cells has been used to indicate the prognosis of AIDS. Serological screening techniques are also being utilized worldwide for the detection of HIV, where the presence of the antibody against HIV antigens, such as the HIV p24 antigen, is detected.

An ELISA assay is currently being utilized on serum samples in most hospitals and screening laboratories to make the determination. However, currently used ELISA assays may not be sensitive enough to detect all HIV infected individuals. This is because that some HIV infected individuals do not have detectable levels of serum antibody to HIV. There may be a significant time lag between detection of HIV infection and seroconversion. In addition, some HIV infected but seronegative individuals might never convert but will remain infected throughout theirs lives. Thus, such a screening method may generate false negatives, which in turn may increases the probability of HIV infection of healthy people by these individuals.

Another method for detecting HIV infection in seronegative individuals was described (Jehuda-Cohen, T. et al. Proc. Natl. Acad. Sci. UAS, 87: 3972–3076 (1990)) wherein peripheral blood mononuclear cells (PBMC) are isolated from the blood and then exposed to a mitogen such as pokeweed mitogen. Incubation of isolated PBMC with pokeweed mitogen caused the PBMC to secret immunoglobulins that were specific for HIV. The failure of the ELISA assay to detect all HIV infected individuals places the population at risk by misleading the HIV infected individuals that they are not infected, thereby making it more likely that the HIV infected individuals will unknowingly infect others.

The existence of HIV has also been determined by using the reverse transcriptase-polymerase chain reaction (RT-PCR) to amplify plasma HIV RNAs (U.S. Pat. No. 5,674,680). This method is used to detect three types of HIV mRNA in peripheral blood cells: unspliced, multiple spliced, and single-spliced mRNA in AIDs patients, HIV-infected but asymptomatic individuals and individuals who are undergoing therapy for AIDS. However, the correlation between the differences in HIV mRNA levels and AIDS prognosis needs to be established.

Many antiviral drugs have been developed to inhibit HIV infection and replication by targeting HIV reverse transcriptase and proteases. Treatment following a prolonged single drug regimen has met with limited success where there is relatively small drop in viral load, followed by a rise in amount of detectable virus in blood, presumably due to the development of drug resistance strains of HIV. The resistance of HIV to drugs is not only associated with the high mutation rates of HIV but also due to the selective pressure of prolonged anti-HIV drug therapy. Since the original description of diminished susceptibility of isolates of HIV-1 to zidovudine (AZT) (Larder et al. Science (1989) 243:1731–1734), the literature has disclosed many descriptions of diminished susceptibility to AZT in different clinical situations, with different assay systems, and of genetic mutations responsible for changes in susceptibility. For example, isolates from subjects not treated with AZT display a narrow range of susceptibilities to AZT, with the 50% inhibitory concentrations (IC50) ranging from 0.001 to 0.04 $\mu$M (Larder et al. (1989), supra; Rooke et al. AIDS (1989) 3:411–415; Land et al. J Infect Dis (1990) 161:326–329; Richman et al. J. AIDS (1990) 3:743–746; Tudor-Williams et al. Lancet (1992) 339:15–19). This narrow range of susceptibilities is typical for HIV isolates from subjects of all ages and at all stages of HIV infection. Isolates of HIV from patients who receive AZT, however, chronically display progressive reductions of susceptibility to AZT over periods of months to years. Diminished susceptibility to AZT of an isolate of HIV-2 from a patient on prolonged therapy has also been reported (Pepin et al. Eighth International Conference on AIDS, Amsterdam, The Netherlands, Jul. 19–24, 1992 Abstract PoA 24401).

In addition to AZT, HIV resistance have been seen with other nucleosides and to nonnucleoside anti-retroviral drugs. For example, isolates resistant to AZT display diminished susceptibility to other nucleosides containing a 3'-azido moiety, including 3'-azido-2',3'-dideoxyuridine, 3'-azido-2', 'dideoxyguanosine, and 3'-azido-2',3'-dideoxyadenosine (Larder et al. (1989), supra; Larder et al. Antimicrob Agents Chemother (1990) 34:436–441). Additionally, AZT-resistant isolates are reported to display cross-resistance to didehydrodideoxythymidine (Rooke et al. Antimicrob. Agents Chemother. (1991) 35:988–991).

Drug resistance in HIV isolates is not limited to inhibitors of reverse transcriptase and virtually all drug targets for anti-HIV therapy are susceptible to the development of resistance. For example, a mutant with resistance to a protease inhibitor has been isolated that exhibits an eightfold reduction in susceptibility to a protease inhibitor (Patterson et al. Eighth International Conference on AIDS, Amsterdam, The Netherlands, Jul. 19–24, 1992, Abstract ThA 1506).

In the last five year, with the fast development of anti-HIV drugs and utilization of combination therapy, treatment of HIV infection with multiple antiviral drugs ("cocktails") have led to diminutions in the amount of viral RNA and virus detectable in blood by using current detection methods. It has been shown that combination therapy with 3 or more antiviral drugs, e.g. indinavir, zidovudine, and lamivudine, or alternatively, nevirapine, zidovudine, and didanosine, in previously untreated patients has resulted in profound decreases in viral burden (Wainberg, M. A. and Friedland, G. JAMA (1998) 279: 1977–1983). It was believed that the combination antiviral regimens used must have blocked viral replication to the extent that the mutations that encode drug resistance could not occur. However, current studies showed that a growing number of patients are failing combination drug regimens (Deek, S. et al. the 5th Conference on Retroviruses and Opportunistic Infection, Chicago, Feb. 1–5, 1998, Abstract #419). Finding an effective salvage therapy for them is difficult.

In the clinical setting, drug resistance is often not detected until a patient manifests symptoms of disease progression, which is generally not observed until significantly after development of a drug resistant strain of virus. Thus, there is a clear need for an assay which can indicate the drug resistance of virus strains so drug therapy for a patient can be modified accordingly, and optimally as soon as resistance is detected rather than delaying until clinical symptoms are observed.

Currently the most commonly used assays for susceptibility of HIV to antiviral drugs involve the measurement of the inhibition of cytopathology, p24 production, or reverse transcriptase production of a laboratory strain of HIV in a lymphoblastoid cell line. Such assays may not be readily applied to clinical isolates of HIV. Examples of commonly used assays of drug susceptibility of clinical isolates have been the syncytial focus assay in CD4-HeLa cells (Chesebro, B. and Wehrly, K., J. Virol. (1988) 62:3779–3788), inhibition of p24 production in primary peripheral blood mononuclear cells, and reverse transcriptase (RT) assays using cultured primary T-cells from patient blood. (Richman et al. In: Current Protocols in Immunology, Coligan et al., eds, (1993) Brooklyn, J. Wiley).

One of the disadvantages associated with the syncytial focus assay is that it may only detect HIVs that exhibit a syncytial-inducing phenotype and that in practice may only be obtained from a minority of specimens from seropositive individuals. And the syncytial focus assays may not be used for screening for drugs that affect posttranslational processing, such as glycosidase and protease inhibitors. On the other hand, the p24 and RT assays may also suffer the limitations of difficult quantification, low sensitivity and unproven clinical validity.

SUMMARY OF THE INVENTION

The present invention provides innovative recombinant vectors, cells containing the vectors, kits and methods using these vectors and cells for detecting and monitoring HIV infection. Assays using the inventive vectors and cells are robust, efficient and sensitive in detection of the presence of HIV, especially in direct detection of clinical isolates of HIV. These assays can be used for early diagnosis of HIV infection, testing HIV replication efficiency, monitoring HIV resistance in patients, and screening for synthetic or natural anti-HIV agents.

In one aspect of the invention, recombinant cells are provided. In one embodiment, the recombinant cell comprises: a reporter sequence introduced into the recombinant cell comprising a reporter gene whose expression is regulated by a protein specific to HIV, the recombinant cell being capable of cell division and expressing a CD4 receptor and one or more additional cell surface receptors which facilitate productive infection of the recombinant cell by the HIV; and the recombinant cell enabling HIV which has infected the recombinant cell to replicate and infect non-infected cells in a culture of the recombinant cell.

In another embodiment, the recombinant cell comprises: a reporter sequence comprising a reporter gene whose expression is regulated by a protein specific to HIV; and a heterologous sequence which encodes CD4 and one or more additional cell surface receptors. The heterologous sequence expresses CD4 and the one or more additional cell surface receptors at elevated levels as compared to the cell in the absence of expression by the heterologous sequence such that productive infection of the recombinant cell by the HIV is achieved, which is defined by HIV viral replication and the infection of non-infected cells in a culture of the recombinant cell.

As used herein, introducing a reporter sequence into a recombinant cell refers to the introduction of a sequence into cell by any of a variety of recombinant methodologies including, but not limited to, transformation, transfection and transduction.

The recombinant cell may optionally express a sufficient number of cell surface receptors to render the recombinant cell permissive to substantially all strains of HIV. Alternatively, the recombinant cell may express a selected group of cell surface receptors such that the recombinant cell is permissive to a selected group of strains of HIV. Examples of cell surface receptors which may be expressed by the recombinant cell include, but are not limited to CXCR4, CCR5, CCR1, CCR2b, CCR3, CCR4, CCR8, CXCR1, CXCR2, CXCR3, CX$_3$CR1, STRL33/BONZO and GPR15/BOB.

The stably transferred reporter sequence may optionally comprise a promoter sequence including an HIV-specific enhancer sequence, and a reporter gene whose expression is regulated by binding of an HIV specific transactivator protein to the HIV specific enhancer sequence. According to this variation, the HIV specific transactivator protein is preferably Tat and the HIV specific enhancer sequence preferably comprises at least one copy of TAR sequence. Alternatively, the HIV specific protein may optionally regulates expression of the reporter sequence by a protein-protein interaction between the HIV specific protein and a transactivator protein present in the recombinant cell.

Examples of the HIV specific protein include, but are not limited to, HIV proteins Tat, Rev, Vpr, Vpx, Vif, Vpu, Nef, Gag, Env, RT, PR, and IN. The HIV specific protein may optionally be an HIV transactivator protein such as Tat.

Expression of the reporter gene in the recombinant cell may be is up-regulated or down-regulated by the HIV specific protein.

In another aspect of the invention, methods are provided for detecting the presence of HIV in a sample. In one embodiment, the method comprises:

taking a culture of recombinant cells which (a) are capable of cell division, (b) express CD4 receptor and one or more additional cell surface receptors necessary to allow the HIV to infect, (c) enable the HIV to replicate and infect the noninfected cells in the cell culture, and (d) comprise a reporter sequence introduced into the recombinant cells comprising a reporter gene whose expression is regulated by a protein specific to HIV;

contacting the cell culture with a sample to be analyzed for the presence of HIV in the sample; and detecting a change in a level of expression of the reporter gene in cells in the recombinant cell culture.

In another embodiment, a method is provided for detecting the presence of different strains of HIV in a sample comprising:

taking a first culture of recombinant cells which (a) are capable of cell division, (b) express CD4 receptor and one or more additional cell surface receptors which render the first cell culture permissive to a first group of strains of HIV but does not render the first cell culture permissive to a second, different group of strains of HIV, (c) enable the HIV to replicate and infect the noninfected cells in the cell culture, and (d) comprise a reporter sequence introduced into the recombinant cells comprising a reporter gene whose expression is regulated by a protein specific to HIV;

taking a second culture of recombinant cells which (a) are capable of cell division, (b) express CD4 receptor and one or more additional cell surface receptors which render the second culture permissive to the second group of strains of HIV but does not render the second cell culture permissive to the first group of strains of HIV, (c) enable the HIV to replicate and infect the noninfected cells in the cell culture, and (d) comprise a reporter sequence introduced into the recombinant cells comprising a reporter gene whose expression is regulated by a protein specific to HIV;

contacting the first and second cell cultures with a sample to be analyzed for the presence of different strains of HIV;

detecting a change in a level of expression of the reporter gene in cells in the first cell culture;

detecting a change in a level of expression of the reporter gene in cells in the second cell culture; and distinguishing between the first and second groups of strains based on whether a change in a level of expression of the reporter gene occurs in the first or the second cell culture.

According to the above method, the first and second cultures of recombinant cells may optionally be mixed with each other. The reporter genes in the first and second cultures of recombinant cells may also optionally be different from each other so that cells of the first cell culture can be distinguished from cells of the second cell culture. This allows different strains of HIV to be detected in a single well containing cells from both cultures.

In yet another aspect of the invention, methods are provided for detecting HIV drug resistance in a sample. The one embodiment, the method comprises:

taking a culture of recombinant cells which (a) are capable of cell division, (b) express CD4 receptor and one or more additional cell surface receptors necessary to allow the HIV to infect, (c) enable the HIV to replicate and infect the noninfected cells in the cell culture, and (d) comprise a reporter sequence introduced into the recombinant cells comprising a reporter gene whose expression is regulated by a protein specific to HIV; contacting the cell culture with a sample containing HIV; adding one or more anti-HIV agents to the cell culture either before or after contacting the cell culture with the sample; and detecting a change in a level of expression of the reporter gene in the cells.

In still another aspect of the invention, methods are provided for taking a patient known to be infected with one or more strains of the HIV and determining what combination of one or more anti-HIV agents would be effective in treating the patient. In one embodiment, the method comprises:

taking a plurality of cell cultures, each of the cultures containing recombinant cells which (a) are capable of cell division, (b) express CD4 receptor and one or more additional cell surface receptors necessary to allow the HIV to infect, (c) enable the HIV to replicate and infect the noninfected cells in the cell culture, and (d) comprise a reporter sequence introduced into the recombinant cells comprising a reporter gene whose expression is regulated by a protein specific to HIV;

contacting the cell cultures with a sample containing the HIV;

adding a different set of one or more anti-HIV agents to each of the cell cultures, either before or after contacting the cell cultures with the sample; and comparing expression of the reporter gene in the plurality of cell cultures.

In still another aspect of the invention, methods are provided for screening compositions for anti-HIV activity. The method comprises:

taking a culture of recombinant cells which (a) are capable of cell division, (b) express CD4 receptor and one or more additional cell surface receptors necessary to allow HIV to infect, (c) enable the HIV to replicate and infect the noninfected cells in the cell culture, and (d) comprise a reporter sequence introduced into the recombinant cells comprising a reporter gene whose expression is regulated by a protein specific to HIV;

contacting the cell culture with a sample containing the HIV;

adding one or more tester agents to the cell culture, either before or after contacting the cell cultures with the sample; and detecting a change in a level of expression of the reporter gene in the cells in the culture.

The tester agents may be any anti-HIV drug candidates from natural sources or synthetically generated. For example, the tester agents may be derived from body fluid or tissues of humans or animals (immunized or naive), such as whole blood, blood serum, isolated peripheral blood cells, T cells, spleens, and bone marrow. The agents can be any agent targeting any components of the HIV, such as reverse transcriptase (RT) inhibitors, protease inhibitors, antisense and ribozyme oligonucleotides against HIV mRNA or viral RNA genome, decoys of TAR sequence or RRE (rev response element), competitive inhibitors like soluble CD4, Gag or Env protein mutants, and agents that bind to HIV receptor or coreceptors and block the entry of HIV into the host cells such as antibodies, either fully assembled, Fab fragments, or single chain antibodies.

For example, the tester agent may be blood serum isolated from an animal (e.g., a human, a primate, and a rodent) immunized with an HIV vaccine, or an antibody or a combination of antibodies isolated from blood serum of an animal immunized with an HIV vaccine.

Optionally, the tester agent may be blood serum isolated from an individual immunized with an HIV vaccine or a candidate vaccine under a clinical trial. The vaccine may be a vaccine specifically targeting a HIV-1 clade such as clade A, B, C, D, E, F, and O, or a vaccine targeting two or more HIV-1 clades. For example, the vaccine may be an adenoviral vector vaccine encoding an antigen from an HIV-1 clade such as clade A, B, C, D, E, F, and O, or encoding two or more antigens from two different HIV-1 clades.

According to any one of the above methods, the recombinant cells in the cell cultures used in the methods may optionally comprise a reporter sequence introduced into the recombinant cells comprising a reporter gene whose expression is regulated by a protein specific to HIV; the recombinant cells being capable of cell division and expressing a CD4 receptor and one or more additional cell surface receptors which facilitate productive infection of the recombinant cell by the HIV; and the recombinant cells enabling the HIV which has infected the recombinant cell to replicate and infect non-infected cells in a culture of the recombinant cell.

Also according to any one of the above methods, the HIV specific protein may be any one of the HIV proteins Tat, Rev, Vpr, Vpx, Vif, Vpu, Nef, Gag, Env, RT, PR, and IN. The HIV specific protein may optionally be an HIV transactivator protein such as Tat.

Also according to any one of the above methods, the reporter sequence may comprise a promoter sequence including an HIV specific enhancer sequence, and a reporter gene whose expression is regulated by binding of an HIV specific transactivator protein to the HIV specific enhancer sequence. In one variation, the HIV specific transactivator protein is Tat and the HIV specific enhancer sequence comprises at least one copy of TAR sequence.

Also according to any one of the above methods, the one or more additional cell surface receptors expressed by the recombinant cell may include, but are not limited to CXCR4, CCR5, CCR1, CCR2b, CCR3, CCR4, CCR8, CXCR1, CXCR2, CXCR3, $CX_3CR1$, STRL33/BONZO and GPR15/BOB.

Also according to any one of the above methods, detecting a change in a level of expression of the reporter gene in the cells may include detecting a change in a level of expression of the reporter gene in individual cells.

Also according to any one of the above methods, detecting a change in a level of expression of the reporter gene in the cells may include detecting a change in a level of expression of the reporter gene across the cell culture.

Also according to any one of the above methods, detecting a change in a level of expression of the reporter gene in the cells may include detecting whether viral replication within the cell culture has occurred.

Also according to any one of the above methods, detecting a change in a level of expression of the reporter gene in the cells may include comparing a level of expression in cells contacted with the sample to a level of expression cells contacted with one or more control samples.

Also according to any one of the above methods, the sample may be any sample which might include HIV including, but not limited to whole blood, blood serum, isolated peripheral blood cells, T cells, and bone marrow. The samples may be clinical isolates from patients that are infected by HIV or laboratory isolates of HIV. The HIV in the sample may be any strain, subtype or clade from any geographic region of the world. Optionally, the HIV in the sample may be HIV-1 clade A, B, C, D, E, F, or O.

Also optionally, the sample containing HIV is a blood sample of an individual infected with HIV and being treated with an anti-HIV drug.

In still another aspect of the invention, kits are provided for performing the various methods of the present invention. These kits may include the cell line of the present invention and any two or more components used to perform these methods.

In one embodiment, the kit comprises: first and second recombinant cell lines, each recombinant cell line comprising: a reporter sequence introduced into the recombinant cells comprising a reporter gene whose expression is regulated by a protein specific to HIV, the recombinant cell line being capable of cell division and expressing a CD4 receptor and one or more additional cell surface receptors which facilitate productive infection of the recombinant cell by the HIV, and the recombinant cell line enabling the HIV which has infected the recombinant cell to replicate and infect non-infected cells in a culture of the recombinant cell; wherein the one or more additional cell surface receptors which the first recombinant cell line expresses renders the first recombinant cell line permissive to a first group of strains of HIV and the one or more additional cell surface receptors which the second recombinant cell line expresses renders the second recombinant cell line permissive to a second, different group of strains of HIV.

According to this embodiment, the first and second recombinant cell lines may optionally be mixed together in the kit. Also according to this variation, the first recombinant cell line may optionally include a first reporter gene and the second recombinant cell line may optionally include a second different reporter gene which allows the first and second recombinant cell lines to be independently identified.

In still another aspect of the invention, recombinant viral vectors are provided for producing the recombinant cell described above. In one embodiment, the recombinant viral vector comprises: a reporter sequence comprising a reporter gene whose expression is regulated by a protein specific to HIV; and a receptor sequence comprising a CD4 gene and one or more coreceptor genes, expression of CD4 and coreceptor genes facilitating productive infection of the transduced cell and enabling the HIV which has infected the transduced cell to replicate and infect non-infected cells in a culture of the cells transduced by the recombinant viral vector.

According to the embodiment, the genes encoding the HIV receptors may be placed under transcriptional control of a constitutive (e.g. CMV and SV40) or an inducible (e.g. tetracycline-inducible) promoter located in the E1 region of the adenoviral vector near the left terminal repeats (L-TR). The reporter sequence may be positioned in the right end of the recombinant adenoviral vector, for example, in the E4 region of the recombinant adenoviral vector near the right terminal repeats (R-TR).

In another embodiment, the recombinant viral vector comprises: a CD4 gene and one or more coreceptor genes, wherein cells transduced by the recombinant viral vector express CD4 and the one or more coreceptor such that productive infection of the recombinant cell by the HIV is achieved. Productive infection is defined by HIV viral replication and the infection of non-infected cells in a culture of the transduced cells.

According to the embodiment, the genes encoding the HIV coreceptors (e.g., CXCR4 and CCR5) may be placed under transcriptional control of a constitutive (e.g. CMV and SV40) or an inducible (e.g. tetracycline-inducible) promoter located in the E1 region of the adenoviral vector near the left terminal repeats (L-TR). The gene(s) encoding CD4 and/or the HIV coreceptors may be positioned in the right end of the recombinant adenoviral vector, for example, in the E3 or E4 region of the recombinant adenoviral vector near the right terminal repeats (R-TR).

In a preferred embodiment, the recombinant viral vector is a recombinant adenoviral vector. The recombinant adenoviral vector may be replication incompetent but carry an adenoviral packaging signal. Optionally, the recombination adenoviral vector has 1–100, 5–80, 10–60, or 20–50 multiplicity of infection (m.o.i.). The vector may carry genes encoding HIV receptors, such as CD4, CXCR4 and CCR5, and optionally, a reporter gene such as β-galactosidase, luciferase, beta-glucuronidase, fluorescent protein (e.g. GFP and BFP), chloramphenicol acetyl transferase (CAT), secreted embryonic alkaline phosphatase (SEAP), hormones and cytokines. The vector may also carry a gene encoding an interleukin (e.g. IL-2 and IL-12) that renders the transduced cells more susceptible to HIV infection. The vector may also carry a eukaryotic polyadenylation sequence such a SV40 polyadenylation site or a BGH polyadenylation site.

Various HIV receptors (or coreceptors)may be transferred into the cells by a single recombinant viral vector carrying all of the HIV receptors, or by multiple recombinant viral vectors, each carrying one or more HIV receptors to confer upon the cell different tropisms.

Alternatively, a recombinant plasmid may be used to introduce the receptor and/or the reporter sequence to the cell. The recombinant plasmid comprises: a reporter sequence comprising a reporter gene whose expression is regulated by a protein specific to HIV; and a receptor sequence comprising a CD4 gene and one or more coreceptor genes, expression of the receptor and coreceptor genes facilitating productive infection of the transfected cell and enabling HIV which has infected the transfected cell to replicate and infect non-infected cells in a culture of the cells transfected with the recombinant plasmid.

The present invention also provides a kit for producing the recombinant cells described above using a recombinant viral vector. In one embodiment, the kit comprises: a recombinant viral vector and a cell line capable of being infected by the vector, the recombinant viral vector comprising a reporter sequence comprising a reporter gene whose expression is regulated by a protein specific to HIV, and a receptor sequence comprising a CD4 gene and one or more coreceptor genes, expression of the receptor and coreceptor genes facilitating productive infection of the transduced cell and enabling HIV which has infected the transduced cell to replicate and infect non-infected cells in a culture of the cells transduced by the recombinant viral vector.

In another embodiment, the kit comprises a recombinant viral vector and a cell line capable of being infected by the vector and comprising a reporter sequence comprising a reporter gene whose expression is regulated by a protein specific to HIV, the recombinant viral vector comprising a CD4 gene and one or more coreceptor genes, wherein the cell line transduced by the recombinant viral vector expresses CD4 and the one or more coreceptor such that productive infection of the recombinant cell by the HIV is achieved. Productive infection is defined by HIV viral replication and the infection of non-infected cells in a culture of the transduced cells.

The present invention also provides a method for producing recombinant cells for detecting a presence of HIV in a sample. The method comprises: taking a culture of cells; and adding a recombinant viral vector into the culture to transduce the cells, the recombinant viral vector comprising a reporter sequence comprising a reporter gene whose expression is regulated by a protein specific to HIV, and a receptor sequence comprising a CD4 gene and one or more coreceptor genes, expression of the receptor and coreceptor genes facilitating productive infection of the transduced cell and enabling HIV which has infected the transduced cell to replicate and infect non-infected cells in the culture of the cells transduced by the recombinant viral vector.

Alternatively, the recombinant cells of the present invention may be produced by transducing cells that already express CD4 and one or more HIV coreceptors such as CXCR4 and CCR5 with a recombinant viral vector containing the reporter sequence. The CD4 and one or more HIV coreceptors may be expressed at levels sufficient for facilitating productive infection of the cells by HIV.

Optionally, the recombinant cells of the present invention may also be produced by transducing cells that already contains the reporter sequence with a recombinant viral vector that expresses CD4 and one or more HIV coreceptors. Upon infection of HIV, expression of the reporter gene on the reporter sequence is activated by a protein specific to HIV (e.g. Tat).

The recombinant cells of the present invention may also be produced by transducing cells that already contains the reporter sequence and CD4 or at least one HIV coreceptor with a recombinant viral vector that expresses CD4 or at least one HIV coreceptor at sufficient levels to facilitate productive infection of HIV in the cells. Upon infection of HIV, expression of the reporter gene on the reporter sequence is activated by a protein specific to HIV (e.g. Tat).

The recombinant viral vector of the present invention may also be used to transduce a cell that expresses CD4 or a coreceptor (e.g. CXCR4 and CCR5) naturally, but at a low level. For example, HUT78 or CEM-NKr-R5 cells express CD4 and a low level of CXCR4. Such cells may be transduced by the recombinant viral vector that contains CD4 or the other coreceptors necessary for productive HIV infection of cells in the culture. Alternatively, the cell may be transfected by a recombinant plasmid according the embodiment described above. By introducing a vector carrying the HIV receptor into the cell, the expression levels of the HIV can be significantly elevated by using strong promoters (such as CMV and SV40 promoters) to overexpress the receptors.

The recombinant viral vector of the present invention may also be used produce cells that express the receptors in a controlled period of time by using an inducible promoter, or in a shorter period of time by using an adenoviral vector. This allows versatile and efficient production of a wide variety of cells which can be used for detecting HIV infection in the cell, screening for anti-HIV drugs and detecting HIV drug resistance in the cells.

Overall, the present invention provides novel recombinant vectors and cell lines, and methods using these cell lines. These methods are convenient, cost-effective and ultra sensitive for the detection of HIV infection and replication. These methods can be very useful for high throughput screening in preclinical drug discovery and development, as well as designing more efficacious anti-HIV drug cocktails in the clinic to combat HIV drug resistance.

BRIEF DESCRIPTION OF THE FIGURES

FIGS. 8A–C show FACS analysis of expression levels of CD4, CXCR4, and CCR5, respectively, in HeLa cells transduced by a recombinant adenoviral vector rAd-R5-X4-D4-X4.

FIGS. 8D–F are photographs of HeLa cells transduced by rAd-R5-X4-D4X4 and stained with fluorescence-labeled antibodies against CD4, CXCR4 and CCR5, respectively.

FIG. 8G is a table summarizing FACS analysis of expression levels of CD4, CXCR4 and CCR5 in HeLa cells transduced with rAd-R5-X4-D4-X4 at different m.o.i. levels, and those of the indicator cell lines developed by others.

FIGS. 9A and 9B show HeLa cells transduced with rAd-R5-X4-D4-X4 in the absence and presence of HIV, respectively.

FIG. 9C shows that antibodies containing in the anti-gp120 antiserum effectively neutralized HIV-1/HTLV-IIIB infection of HeLa cells transduced with rAd-R5-X4-D4-X4.

FIG. 10 shows Table 1 summarizing the results of the tests of susceptibility of the inventive indicator cells to infection of various HIV subtypes (or clades) and the ability of an anti-gp120 antiserum to neutralize infection these subtypes (or clades) of HIV in the indicator cells.

FIG. 11 shows a table comparing i.p. per ml of cultures of indicator cells infected by a laboratory-adapted strain (HIV-1/HTLV-IIIB) of HIV and HIV patient isolates.

DETAILED DESCRIPTION OF THE INVENTION

Figure 1:
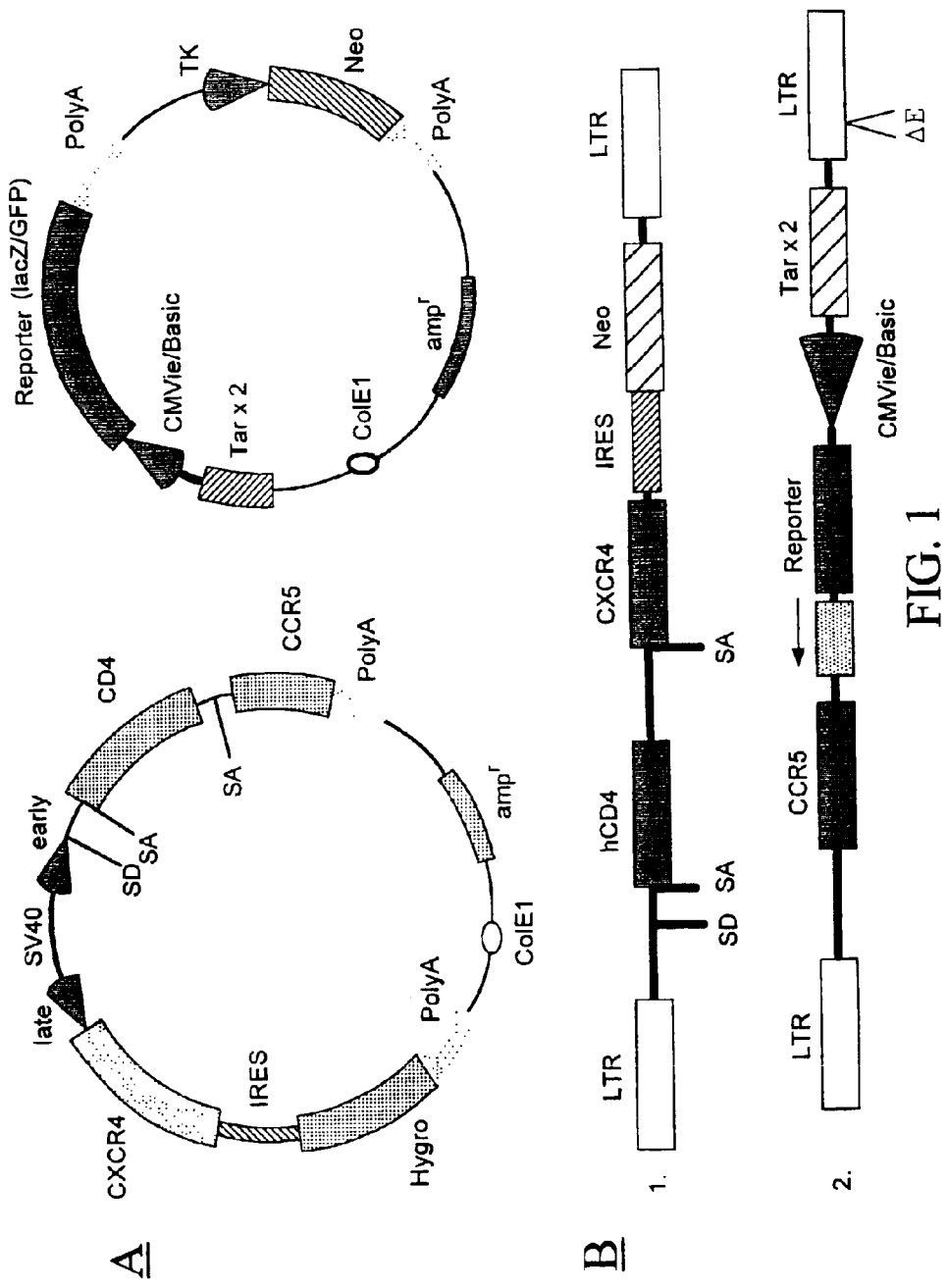
FIG. 1A illustrates expression plasmids for HIV receptors and a reporter gene.
FIG. 1B illustrates retroviral vectors for HIV receptors and a reporter gene.

The present invention relates to new and useful methods including methods for detecting HIV, methods for detecting HIV drug resistance, methods for designing patient customized anti-HIV drug cocktail treatments, and methods for screening compositions for anti-HIV activity. Also provided are novel vectors and cell lines which may be used with the methods of the present invention.

Innovative approaches are employed in the present invention to render recombinant cells susceptible to productive infection of virtually all strains, subtypes or clades of HIV, either in clinical or laboratory isolates of diverse phenotype and co-receptor preference, from any geographic regions of the world. Novel recombinant vectors, including complex viral vectors, are used to transduce a wide variety of cells or cell lines such as tumor cell lines to produce such recombinant cells in large quantity and efficiently. Infection of the recombinant cells by HIV triggers HIV-specific expression of a reporter gene contained in the cells. The recombinant cells can be used as sensitive indicator cells for the detection and monitoring of HIV infection, as well as screening for anti-HIV activity of natural or synthetic agents, in a robust and high throughput manner. The sensitivity of the recombinant cells to HIV infection is further improved by incorporating a bioengineered molecular switch which effectively reduces the background expression of the reporter gene.

In general, the methods of the present invention use recombinant cells which (a) are capable of cell division; (b) are permissive to HIV; (c) express a reporter gene whose expression is selectively regulated by infection with HIV; and (d) allow viral replication of HIV in infected cells which enables cells within the same cell culture which are initially uninfected to become infected. The recombinant cells are rendered permissive to HIV by expressing cell surface receptors such as CD4, CXCR4 and CCR5. The recombinant cell may be generated by transfecting the cell with several plasmids or vectors individually carrying the reporter gene and receptor genes. Alternatively, the recombinant cell may be generated by transfecting the cell with a single plasmid or a replication incompetent viral vector carrying both the reporter gene and genes for HIV receptor (CD4) and coreceptors (e.g. CXCR4 and CCR5).

The inventors believes that levels of the HIV receptor expressed in the cells correlate with the susceptibility of the cells to productive infection of HIV, especially clinical isolates of HIV. Assays for detecting HIV infection using the cell lines developed by others suffer from insensitivity or are only sensitive to laboratory-adapted strains of HIV. For example, cell lines expressing endogenous CD4 and CXCR4 are quite insensitive to infection of clinical isolates of HIV that are most relevant in the diagnosis and monitoring of HIV infection in practice. Others have used mitogen-stimulated human peripheral blood cells (PBMCs) which express endogenous HIV receptors for detecting HIV infection by using techniques such as reverse transcriptase (RT) assay, by a $TCID_{50}$ endpoint titration, or mainly by measuring p24 antigen production by ELISA. These methods are labor-intensive, time-consuming, expensive, and, in the case of the RT assay, requires the use of radioisotopes. In addition, they also require a constant supply of PBMCs cultured from healthy human donors. Use of PBMCs has resulted in variable results due to donor-to-donor variation. Other concerns have been the effort and expense involved in the isolation and culture of PBMCs and the fact that it takes 4 to 10 days to generate a viral end-point because of the kinetics of virus replication and virus spread throughout the PBMC culture.

One of the advantages provided by the present invention is that the recombinant cells used are capable of cell division. As a result, it is easy to produce and maintain these cells for performing the various methods of the present invention.

A further advantage provided by the present invention is that the recombinant cells can be infected by multiple different strains of HIV, including wild-type and mutant HIV strains from clinical isolates or laboratory-adapted strains. As a result, the methods of the present invention have broad applicability to virtually all strains, subtypes or clades of HIV from any geographic regions of the world.

Yet a further advantage provided by the present invention is that infection of the recombinant cells by an HIV can be easily monitored and measured. By using a reporter gene (e.g., a gene encoding a fluorescent protein) whose expression is regulated by infection with HIV, it is possible to detect HIV infection by simple detection methods, such as calorimetric methods, in an efficient and high throughput manner. By expression of the reporter gene being selectively regulated by infection with HIV, false positive signals, for example due to infection by non-HIV, are reduced. The sensitivity of the recombinant cells to HIV infection can also be improved by incorporating in the cells a bioengineered molecular switch that is composed of an HIV-specific enhancer sequence comprising multiple copies of the HIV TAR sequence to achieve a tighter control of the downstream reporter gene in response to HIV infection.

A further advantage of the present invention is that the recombinant cells not only allow entry and infection of the HIV, but also facilitate efficient replication within the recombinant cell and transmission of the mature HIV virion to infect other cells in the culture. By using a cell line in which HIV is able to infect some cells in a cell culture, replicate, and then infect other cells in the cell culture, as well as by coupling viral replication with cell division, the signal produced by the reporter gene is amplified since more cells are infected than would be infected absent replication of HIV within the cell culture. For example, a single virion contained in a sample is ultimately able to infect all cells in the cell culture. This feature allows for sensitive detection of the HIV contained in a sample that is applied to the recombinant cell culture.

By exploiting the above-described advantages, as well as features further described in details below, the recombinant cell line can be used in a variety of methods or assays for many laboratory and clinical applications relating to HIV.

It should be noted that the methods and cells of the present invention can be modified and adapted for various viruses other than HIV, including but are not limited to retroviruses, coronaviruses, herpes viruses and adenoviruses. For example, an immortalized cell line can be constructed to comprise a panel of receptors and coreceptors to allow infection, replication and amplification of one or more strains of a target virus; and a reporter gene whose expression is regulated by a specific gene product expressed by the target virus.

1. Recombinant Cell Line

One aspect of the present invention relates to recombinant cells for use in detecting infection by an HIV. In one embodiment, the recombinant cell comprises:

a reporter sequence introduced into the recombinant cells comprising a reporter gene whose expression is regulated by a protein specific to HIV;

the recombinant cell being capable of cell division and expressing a CD4 receptor and one or more additional cell surface receptors which facilitate productive infection of the recombinant cell by the HIV; and the recombinant cell enabling the HIV which has infected the recombinant cell to replicate and infect non-infected cells in a culture of the recombinant cell.

Regulation of the reporter gene expression may involve up-regulation where the HIV specific protein causes expression of the reporter gene to begin or to increase. Alternatively, regulation of the reporter gene expression may involve down-regulation where the HIV specific protein causes expression of the reporter gene to cease or to decrease.

The HIV specific protein may be an HIV transactivator proteins such as Tat, an HIV regulatory protein such as Rev, HIV accessory proteins such as Vpr, Vpx, Vif, Vpu and Nef, HIV structural proteins such as Gag and Env, or HIV enzymatic proteins such as RT (reverse transcriptase), PR (protease) and IN (integrase). The regulation of the reporter sequence may be achieved by using various methods known in the art. For example expression of the reporter sequence can be regulated by direct binding of the transactivator protein Tat to an enhancer sequence upstream comprising at least one copy of TAR sequence. Alternatively, expression of the reporter gene can be regulated via protein-protein interaction between the HIV specific protein and a transactivator protein present in the recombinant cell.

In one variation of this embodiment, the reporter sequence in the recombinant cell comprises a promoter sequence including an HIV specific enhancer sequence, and a reporter gene whose expression is regulated by binding of an HIV specific transactivator protein to the HIV specific enhancer sequence.

According to this preferred embodiment, regulation of the reporter gene expression in the recombinant cells is achieved by using a promoter sequence including an HIV specific enhancer sequence which is transcriptionally responsive to an HIV specific transactivator protein. Upon infection by the HIV, the HIV specific transactivator protein expressed from the HIV genome binds to the HIV specific enhancer sequence and enhances expression of the reporter gene. The presence, absence or level of the reporter gene product is detected and used to indicate the infection of the HIV.

In a particularly preferred variation, the reporter sequence comprises at least one copy of TAR sequence as the HIV specific enhancer sequence. Expression of the reporter sequence is regulated by the binding of the HIV specific transactivator protein Tat to the enhancer sequence TAR.

A wide variety of reporter genes may be used in the present invention. Examples of proteins encoded by reporter genes include, but are not limited to, easily assayed enzymes such as β-galactosidase, luciferase, beta-glucuronidase, chloramphenicol acetyl transferase (CAT), secreted embryonic alkaline phosphatase (SEAP), fluorescent proteins such as green fluorescent protein (GFP), enhanced blue fluorescent protein (EBFP), enhanced yellow fluorescent protein (EYFP) and enhanced cyan fluorescent protein (ECFP); and proteins for which immunoassays are readily available such as hormones and cytokines. The expression of these reporter genes can also be monitored by measuring levels of mRNA transcribed from these genes.

The one or more additional cell surface receptors expressed by the recombinant cell may optionally include, but are not limited to, CXCR4, CCR5, other chemokine receptors such as CCR1, CCR2b, CCR3, CCR4, CCR8, CXCR1, CXCR2, CXCR3, CX$_3$CR1, and chemokine receptor-like orphan proteins such as STRL33/BONZO and GPR15/BOB.

The presence of CD4 and these one or more additional cell surface receptors allows efficient entry, infection and replication of HIV strains with different tropisms. By causing the recombinant cell to express as many cell surface receptors as possible, the recombinant cell may be rendered permissive to virtually all strains of HIV, regardless of tropism. This may be accomplished by transfecting or transducing the cell with all cell surface receptors known to be involved in HIV infection or by cell fusion with cells, such as T-cells or monocytes, which express these receptors on the cell surface.

Alternatively, by causing the recombinant cell to express certain cell surface receptors or sets of cell surface receptors, it is possible to design the recombinant cell to be permissive to certain strains of HIV and to not be permissive to other strains of HIV. Thus, by selecting which cell surface receptors are expressed, cell lines can be designed for screening for particular strains or groups of strains of HIV.

Compared to human T-cells that have been used in the art for HIV production, the recombinant cell lines of the present invention are relatively easier to culture, more stable, and less expensive. It has been acknowledged that the principle cell types targeted by HIV-1 are helper T-lymphocytes and cells of the monocyte macrophage lineage via the CD4 receptor pathway in vivo, while in tissue culture systems, HIV are cytopathic for CD4$^+$-lymphocytes and cause dysfunction of macrophages, which is directly accounted for depletion of T cells in the body. Since replicating HIV in infected individuals is readily detected in peripheral blood and lymph lodes, human peripheral mononuclear cells (PBMC), in particular, have been frequently used as host cells for HIV infection in vitro and anti-HIV drug-susceptibility testing. One of the disadvantages with PBMC cells is that these primary cells have to be obtained from donors, carefully cultured and freshly prepared each time. It is costly and inefficient to use these primary T-cells for commercial purposes. In addition, the permissiveness of these T-cells to different strains of HIV may vary with the donor, thus causing ambiguity in clinical testing. Thus, the recombinant cells of the present invention which can be produced in an ample supply, are permissive to HIV infection, relatively stable and can be cultured and manipulated more easily in vitro, are well suited for large scale commercial reproduction and use in high throughput screening.

2. Methods for Detecting HIV in a Sample

Methods are provided for detecting a presence of HIV in a sample. In one embodiment, the method comprises:

taking a culture of recombinant cells, which (a) are capable of cell division, (b) express CD4 receptor and one or more additional cell surface receptors necessary to allow the HIV to infect, (c) enable the HIV to replicate and infect the noninfected cells in the culture, and (d) comprise a reporter sequence introduced into the recombinant cells comprising a reporter gene whose expression is regulated by a protein specific to HIV;

contacting the cell culture with a sample to be analyzed for the presence of HIV in the sample; and detecting a change in a level of expression of the reporter gene in cells in the culture, such change being indicative of the HIV being present in the sample and infecting cells in the cell culture.

The culture of recombinant cells used in the method may be any cell culture which has the above described properties. The recombinant cells described in Section I are examples of cells having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in cells contacted with the sample to a level of expression cells contacted with one or more control samples. For example, cells contacted with a sample not containing HIV can serve as a negative control, while cells contacted with a sample containing HIV, recombinant and stabilized HIV, or another virus capable of infecting the cells and causing expression of the HIV specific protein, such as a modified adenovirus encoding Tat, can serve as a positive control. By using suitable controls, induction of the reporter gene expression may be better correlated with HIV infection.

The present invention also provides a method for producing recombinant cells and then detecting a presence of HIV in a sample. In one embodiment, the method comprises:

taking a culture of cells;

adding a recombinant viral vector into the culture to transduce the cells, the recombinant viral vector comprising a reporter sequence, comprising a reporter gene whose expression is regulated by a protein specific to HIV, and a receptor sequence comprising a CD4 gene and one or more coreceptor genes, expression of the receptor and coreceptor genes facilitating productive infection of the transduced cell and enabling HIV which has infected the transduced cell to replicate and infect non-infected cells in the culture of the cells transduced by the recombinant viral vector;

contacting the cell culture with a sample to be analyzed for the presence of HIV in the sample; and detecting a change in a level of expression of the reporter gene in cells in the culture.

In another embodiment, the method comprises:

taking a culture of cells containing a reporter sequence comprising a reporter gene whose expression is regulated by a protein specific to HIV;

adding a recombinant viral vector into the culture to transduce the cells, the recombinant viral vector comprising a CD4 gene and one or more coreceptor genes, expression of the receptor and coreceptor genes facilitating productive infection of the transduced cell and enabling HIV which has infected the transduced cell to replicate and infect non-infected cells in the culture of the cells transduced by the recombinant viral vector;

contacting the cell culture with a sample to be analyzed for the presence of HIV in the sample; and detecting a change in a level of expression of the reporter gene in cells in the culture.

According to the method, the recombinant cells may be produced by transducing the cells with adenoviral vectors containing both the reporter gene and the receptor genes, or by transducing cells which already contain the reporter sequence with adenoviral vectors containing the receptor genes. Expression of these genes are episomal and thus results in minimum genotoxicity. In addition, adenoviral expression in the transduced cell is stable for a relatively long period of time (~weeks), allowing enough time for various manipulation of the cells, such as the use for detecting a presence of HIV in a sample of a patient. Examples of such recombinant viral vectors are described in Section 6.

The present invention also provides a method for detecting a presence of HIV in a culture of cells that are already infected by HIV or can be infected by HIV. The method comprises:

taking a culture of cells that are capable of facilitating productive infection of the cells and enabling HIV which has infected the cells to replicate and infect non-infected cells in the culture of the cells;

adding a recombinant viral vector into the culture to transduce the cells, the recombinant viral vector comprising a reporter sequence, comprising a reporter gene whose expression is regulated by a protein specific to HIV which is expressed from a genome of an HIV upon infection of the cells in the culture; and detecting a level of expression of the reporter gene in cells in the culture.

According to this method, the cells may or may not be recombinant. For example, a stable cell line derived from PBMC can be susceptible to infection of HIV. Such a cell may already be infected by HIV or can be infected by HIV added into the cell culture. After the cell is transduced by the recombinant viral vector, expression of the reporter gene carried by the viral vector can be regulated by a protein specific to HIV, such as Tat, which can be detected by measuring the level of expression of the reporter gene.

It is noted that regulation of the reporter gene may be up regulation or down regulation. Accordingly, a change in the level of expression of the reporter gene may be an increase or decrease in reporter gene expression.

The methods described above can be used for diagnosis of HIV contained in variety of samples including, but are not limited to, whole blood, blood serum, isolated peripheral blood cells, T cells, other biological fluids such as urine, saliva, tears and semen, as well as isolated wild-type or mutant HIV from laboratories or clinics. For example, whole blood of individuals can be tested for the presence of HIV by using the methods described above. In addition, blood or bone marrow samples from individual donors or samples from pooled blood stored in blood banks can be screened for the presence of HIV. The sensitivity of the methods to detect even a single HIV virion allows for the diagnosis of HIV in individuals at a very early stage of HIV infection and can be used to prevent HIV-positive blood from being transfused into patients.

One advantage of using the above-described method for HIV diagnosis is attributed to the specific response of the recombinant cells to HIV only. Because expression of the reporter gene is specifically regulated by HIV specific gene products, ambiguity in diagnosis or report of false positives can be avoided in the clinic. On the other hand, by using the above-described method, HIV may be detected in those individuals who are infected by HIV but do not have detectable levels of serum antibody (seronegatives), thereby reducing the incidents of false negatives which may arise from using antibody-based detection methods.

The methods described above can also be used to amplify HIV, especially strains with low occurrences in the blood sample and evasive to other detections. With the replication and amplification of the HIV in the recombinant cells, HIV with higher titer can be generated in the cell culture and isolated for further studies such as cloning of novel HIV strains.

The methods described above can also be used to differentiate strains or tropisms of HIV in a sample by using recombinant cells selectively expressing certain HIV coreceptors. For example, CXCR4 coreceptor which is required by T-tropic strains can be selectively expressed in a first recombinant cell line to allow infection of T-tropic strains of HIV. Meanwhile, since M-tropic strains require CCR5 coreceptor to infect cells, a second recombinant cell line can be constructed to selectively express CCR5 to allow infection of M-tropic strains of HIV. By having the first and second recombinant cell lines expressing different coreceptors, the first and second recombinant cell lines can selectively detect T-tropic, M-tropic or dual-tropic strains in the presence of other strains of HIV.

Alternatively, the first recombinant cell line may include a first reporter gene such as GFP, while the second recombinant cell line may include a second reporter gene such as EBFP. When the first and second cell lines are mixed in one culture and contacted by a sample containing HIV with unknown tropism, selective expression of one reporter gene may indicate single tropism of the virus, while expression of both reporter genes may indicate dual tropism. Different fluorescences emitted by the first and second cell lines observed under microscope can facilitate independent identification of each cell line in one culture.

The methods described above can also be used for quantitative analysis of HIV in a sample. For example, by using control samples with varying titers, the viral load can be readily calculated by comparing to the control samples. Alternatively, the viral titer of a sample can also be determined by serially diluting the sample until end point infection is achieved in multiple cell culture plates, i.e. some of the cell culture plates are infected while the other plates are not infected by the diluted sample.

3. Methods for Detecting HIV Drug Resistance

Methods are also provided for detecting HIV drug resistance in a sample. These methods may be used to detect whether a course of treatment for HIV infection with one or more drugs is ineffective due to the presence of one or more strains of HIV which are resistant to the one or more drugs being used. These methods may also be used to isolate HIV strains which are resistant to one or more anti-HIV agents.

In one embodiment, the method comprises:

taking a culture of recombinant cells, which (a) are capable of cell division, (b) express CD4 receptor and one or more additional cell surface receptors necessary to allow the HIV to infect, (c) enable the HIV to replicate and infect the non-infected cells in the culture, and (d) comprise a reporter sequence introduced into the recombinant cells comprising a reporter gene whose expression is regulated by a protein specific to HIV;

contacting the cell culture with a sample containing HIV;

adding one or more anti-HIV agents to the cell culture either before or after contacting the cell culture with the sample; and detecting a change in a level of expression of the reporter gene in the cells.

In another embodiment, a method is provided for detecting HIV drug resistance in a sample. The method comprises:

taking a culture of cells that are infected by HIV, the cells being capable of facilitating productive infection of the cells and enabling HIV which has infected the cells to replicate and infect non-infected cells in the culture of the cells;

adding a recombinant viral vector into the culture to transduce the cells, the recombinant viral vector comprising a reporter sequence, comprising a reporter gene whose expression is regulated by a protein specific to HIV;

adding one or more anti-HIV agents to the cell culture; and detecting a change in a level of expression of the reporter gene in cells.

According to this embodiment, the cells may or may not be recombinant. Prior to transduction of the cells with recombinant viral vector, the cells are already infected by HIV or can be infected by adding HIV into the cell culture. After the cells are transduced by the recombinant viral vector, expression of the reporter gene carried by the vector can be regulated by a protein specific to HIV such as Tat. Detection of the change in the level of reporter gene expression in the presence and absence of the anti-HIV agent should provide information on HIV resistance to such an agent.

Anti-HIV agents used in the methods may be any agents with known anti-HIV activities, either tested preclinically or clinically. Examples of anti-HIV agents which may be used to screen for HIV drug resistance include, but are not limited to, nucleoside HIV RT inhibitors such as ZIDOVUDINE, DIDANOSINE, ZALCITABINE, LAMIVUDINE, STAVUDINE, ABACAVIR, nonnucleoside RT inhibitors such as NEVIRAPINE, DELAVIRDINE, EFAVIRENZ, protease inhibitors such as INDINAVIR, RITONAVIR, SAQINAVIR, NELFINAVIR, AMPRENAVIR, HIV integrase inhibitors, HIV fusion inhibitors and combinations thereof.

The culture of recombinant cells used in the method may be any cell which has the above described properties. The recombinant cells described in Section I are examples of cells having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in cells contacted with the sample to a level of expression cells contacted with one or more control samples. For example, cells contacted with a sample containing HIV but not with the one or more anti-HIV agents can serve as a negative control, while cells contacted with a sample containing a HIV that is not known to be resistant to the one or more anti-HIV agents added may preferably serve as a positive control. By using suitable controls, induction of the reporter gene expression may be better correlated with the resistance of the HIV to the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more anti-HIV drugs before being contacted with a sample containing the HIV. Alternatively, the cell culture may be contacted with one or more anti-HIV drugs after being contacted with a sample containing the HIV and incubating for a time sufficient for the HIV replication to occur. This may be particularly advantageous for the initial amplification of the HIV with low titer in the sample before being tested for drug resistance.

The methods described above can be used to detect drug resistance of HIV contained in patient samples, isolated virus stocks or laboratory-adapted HIV strains. Owing to ultra sensitivity of the recombinant cells to a single HIV virion, the strains of HIV that escape the drug regimen or the ones that are not predominant circulating variants can replicate in the cell culture and be isolated for further genotypical analysis.

In comparison, the methods that have been used to detect anti-HIV drug resistance are less sensitive, time-consuming and technically demanding. The currently used methods include genotypic assays for detecting HIV genome mutation based on PCR amplification of the viral RNA followed by sequencing of the amplified DNA templates, and phenotypic assays based on recombinant HIV (Hirsch, M. S. (1998) JAMA 279: 1964–1991). While the most sensitive PCR-based assay that has been developed may not be sensitive enough to detect plasma HIV RNA below 50 copies/mL, false positivity for mutations may be generated due to carry over from other HIV samples in the laboratory or from random polymerase errors during PCR. The recombinant virus assay requires a first RT-PCR amplification of plasma HIV RNA at more than 1000 copies/mL, cloning the viral cDNA into an HIV vector, and then growing up the virus in permissive cell line. The whole process may take more than two weeks to generate results and demand for highly skilled personnel to perform the test.

Thus, the methods provided in the present invention are more sensitive for detecting replicating HIV (at only about 5 virions/mL), more efficient for testing for HIV drug resistance (less than a week), and more economic for high throughput screening.

4. Methods for Designing Patient Customized HIV Cocktail Treatments

Methods are also provided for taking a patient known to be infected with one or more strains of the HIV and determining what combination of one or more anti-HIV agents will be effective in treating the patient. These methods can be used when a patient is initially being treated with anti-HIV agents or after a patient has been treated for a period of time with one or more anti-HIV agents and one or more resistant strains may have developed resistance to the anti-HIV agents being used.

In one embodiment, the method comprises:

taking a plurality of cell cultures, each of the cultures containing recombinant cells (a) are capable of cell division, (b) express CD4 receptor and one or more additional cell surface receptors necessary to allow the HIV to infect, (c) enable the HIV to replicate and infect the noninfected cells in the culture, and (d) comprises a reporter sequence introduced into the recombinant cells comprising a reporter gene whose expression is regulated by a protein specific to HIV;

contacting the cell cultures with a sample containing the HIV;

adding a different set of one or more anti-HIV agents to each of the cell cultures, either before or after contacting the cell cultures with the sample; and comparing expression of the reporter gene in the plurality of cell cultures.

In one variation, each cell culture of the plurality is contacted with a different set of one or more anti-HIV agents before being contacted with a sample containing the HIV.

In another variation, each cell culture of the plurality is contacted with a different set of one or more anti-HIV drugs after being contacted with a sample containing the HIV and incubating for a time sufficient for the HIV replication to occur.

The anti-HIV agents can be any agents with known anti-HIV activities, such as the ones described in Section 3, and combinations thereof.

The culture of recombinant cells used in the method may be any cell which has the above described properties. The recombinant cells described in Section I are examples of cell having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In yet another variation of this embodiment, the method further includes comparing the change in the level of expression of the reporter gene when different or no anti-HIV agents are used. For example, a recombinant cell culture that is contacted with the sample containing the HIV but not with the one or more anti-HIV agents can serve as a negative control, while a recombinant cell culture that is contacted with a sample containing HIV or a modified adenovirus, and the one or more anti-HIV agents can serve as a positive control. By using suitable controls, inhibition of the reporter gene expression may be better correlated with anti-HIV efficacy of the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more anti-HIV agents before being contacted with a sample containing the HIV. Alternatively, the cell culture may be contacted with one or more anti-HIV agents after being contacted with a sample containing the HIV and incubating for a time sufficient for the HIV replication to occur. Such preamplification of the HIV may be advantageous for patient samples containing lower titer of the HIV to be tested against the anti-HIV agents.

The methods provided in this section can be used for screening an anti-HIV agent or agent combinations that are most active in inhibiting HIV viral infection and/or replication. The screening can be conducted against virtually all strains of HIV, regardless of their genotypes or tropisms. The results generated can help the physician of HIV infected patients monitor HIV drug resistance, optimize the drug regimen and use the most efficacious drug "cocktail" to treat the patient. By using such drug cocktails customized for each individual patient and adjusted during the course of the treatment, physicians may successfully prevent the HIV from developing drug resistance. Furthermore, physicians can avoid unnecessary side effects and drug toxicity that would otherwise arise from treating a patient with ineffective anti-HIV agents.

The ample and stable supply of the recombinant cells used in these methods, as well as the ease of culturing the cells, enables one to use the methods provided in this, section in a high throughput screening format to test many more drug cocktail combinations than would otherwise have been possible. Furthermore, because the HIV contained in the sample from a patient may potentially harbor drug resistances strains, conventional drug screening may not have been effective in finding the optimum drug regimen. By using the methods provided in this section, the most efficacious drug regimen may be readily identified by designing and testing exhaustive combinations of different drugs that target different components of the HIV or HIV receptors.

5. Methods for Screening Compositions for Anti-HIV Activity

The present invention also relates to methods for screening compositions which are not known to have anti-HIV activity for anti-HIV activity. As used herein, a composition is intended to refer to any composition of matter, including single molecules, macromolecules such as proteins and nucleotides, or combinations of two or more molecules or macromolecules.

In one embodiment, the method comprises:

taking a culture of recombinant cells, which (a) are capable of cell division, (b) express CD4 receptor and one or more additional cell surface receptors necessary to allow the HIV to infect, (c) enable the HIV to replicate and infect the noninfected cells in the culture, and (d) comprise a reporter sequence introduced into the recombinant cells comprising a reporter gene whose expression is regulated by a protein specific to HIV;

contacting the cell culture with a sample containing the HIV;

adding one or more tester agents either before or after contacting the cell cultures with the sample; and detecting a change in a level of expression of the reporter gene in the cells in the culture.

The culture of recombinant cells used in the method may be any cell culture which has the above described properties. The recombinant cells described in Section I are examples of cells having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in a sample to a level of expression in one or more control samples. For example, a recombinant cell culture that is contacted with a sample containing HIV but not with any potentially anti-HIV agents can serve as a negative control, while a recombinant cell culture that is contacted with a sample containing an HIV and the one or more agents that are known to have anti-HIV activity can serve as a positive control. By using suitable controls, regulation of the reporter gene expression may be better correlated with anti-HIV efficacy of the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more tester agents before being contacted with a sample containing the HIV. Alternatively, the cell culture may be contacted with one or more agents after being contacted with a sample containing the HIV and incubating for a time sufficient for the HIV replication to occur. This may be particularly advantageous for the initial amplification of the HIV with low titer in the sample before being tested against the agents.

The tester agents may be any anti-HIV drug candidates from natural sources or synthetically generated. For example, the tester agents may be derived from body fluid or tissues of humans or animals (immunized or naive), such as whole blood, blood serum, isolated peripheral blood cells, T cells, spleens, and bone marrow. The agents can be any agent targeting any components of the HIV, such as reverse transcriptase (RT) inhibitors, protease inhibitors, antisense and ribozyme oligonucleotides against HIV mRNA or viral RNA genome, decoys of TAR sequence or RRE (rev response element), competitive inhibitors like soluble CD4, Gag or Env protein mutants, and agents that bind to HIV receptor or coreceptors and block the entry of HIV into the host cells such as antibodies, either fully assembled, Fab fragments, or single chain antibodies.

For example, the methods described above can be used as a neutralization assay for studying and identifying candidate vaccines that contain or encode neutralizing antigens. The tester agent used in the methods may be whole blood or serum of a human or a nonhuman animal immunized with the candidate vaccine.

The recombinant indicator cells of the present invention can be adapted to possess all of the characteristics required for a vastly improved cell culture-based HIV-1 neutralization assay: for example, (1) the transduced cell line is human, (2) it over-expresses CD4, CXCR4, and CCR5 at levels which are broadly comparable to or in excess of those of activated PBMCs so that the cells are permissive to all HIV-1 laboratory strains and clinical isolates of diverse phenotype and co-receptor preference, (3) the sensitive Tat-activated molecular switch controlling a GFP reporter allows for ready quantification of HIV-1 with a rapid, yet simple fluorescent focus unit (ffu) end-point, equated to infectious particle (i.p.) count, that can be measured with simple 96-well plate-reader instrumentation. Thus, the inventive indicator cells provide a means for high-throughput processing and screening of multiple samples for high-capacity performance of HIV-1 infectivity (viral load)/drug susceptibility/neutralization assays. The neutralization assay can be performed using a very low viral inoculum size because of its improved sensitivity for the detection of low level HIV-1 infection, so that it should be extremely sensitive in detecting neutralizing antibodies in patients' sera and should have a wide dynamic range.

In particular, the recombinant cells of the present invention can be used to identify which strain(s), subtype(s) or clade(s) of HIV the candidate vaccine can elicit neutralizing antiserum or antibody against. To standardize such a neutralization assay for use with broadly reactive antisera, a series of clade-specific vaccines may be constructed for producing the clade-specific neutralizing antisera against each specific clade. The clade-specific antibodies can be used as a series of positive controls to block clade-specific HIV-1 infection, but with very low cross-reactivity with viruses from different clades. For example, native or modified gp160 genes of the HIV-1 clade A, B, C, D, E, F, G, and O may incorporated into adenoviral vectors for clade-specific vaccine production. To increase the HIV-1 envelope expression and antigenic protein stability, gp160 may be modified by deleting the cleavage site between gp120 and gp41 and truncating the C-terminal of gp41 to generate clade-specific, modified envelope ($Env^m$). The modified envelope may be cloned into adenoviral shuttle vectors, pLAd and pRAd, to generate the pLAd-$Env^m$ and pRAd-$Env^m$. The pLAd-$Env^m$ and pRAd-$Env^m$ can then be ligated with the adenoviral backbone to produce the complex defective recombinant adenoviral vaccine. These adenoviral vaccines can be used to immunize animals by expressing multiple isolate- and clade-specific vaccinating antigens for the production of broadly neutralizing HIV-1 antisera. The antisera can then be used as the tester agents in the above-described neutralization assays to select the most important antigenic epitopes for neutralization. These pooled antigens may be used to immunize animals for the production of broadly neutralizing antisera against all HIV-1 isolates and clades, as well as for use in the standardization of the neutralization assay for use with all clinical isolates, regardless of phenotype or co-receptor preference, and with viruses from all clades and geographic regions of the world.

Compared with PBMC-based assay for HIV detection, the sensitivity of the neutralization assay described above may be more sensitive in the evaluation of candidate HIV-1 vaccines for the induction of broadly neutralizing antibodies against all primary clinical isolates of all sub-types or clades and collected from all geographic areas of the world. The neutralization assay of the present invention represents a significant improvement in the laboratory technology available for HIV vaccine research and development and HIV vaccine evaluation programs worldwide.

The methods described above can also be used for high throughput screening for anti-HIV drug candidates against various HIV containing samples, especially for libraries of compounds generated by combinatorial chemistry. These methods may be performed in any format that allows rapid preparation and processing of cells contained in multiple-well plates, such as 96-well plates. Stock solutions of the test agent as well as other assay reagents may be prepared manually and all subsequent pipetting, diluting, mixing, washing, incubating, sample readout and data collecting may be done using commercially available robotic pipetting equipment, automated work stations, analytical instruments for detecting the signal generated by the assay. Examples of such detectors include, but are not limited to, spectrophotometers, calorimeters, luminometers, fluorometers, and devices that measure the decay of radio-isotopes.

The methods described above are particularly cost-effective for use in high throughput screening because the recombinant cells are immortalized, easy to culture and more stable, compared to primary human cells such as PBMC cells. Furthermore, effects of multiple agents at multiple doses on HIV infection and replication can be directly monitored by detecting levels of reporter gene products in the 96-cell culture plates on a calorimetric or fluorescence plate reader.

6. Construction of Recombinant Cell Lines According to the Present Invention The recombinant cell lines used in the present invention can be constructed by using a variety of methods. The recombinant cell may be constructed by transfecting a host cell with several plasmids or vectors individually carrying the reporter gene and receptor genes. Alternatively, the recombinant cell may be generated by transfecting the host cell with a single plasmid or a replication incompetent viral vector carrying both the reporter and the receptor genes.

a) Host Cell Lines

The recombinant cell lines used in the present invention can be constructed from a wide variety of immortalized cell lines. In one embodiment, the recombinant cells are immortalized tumor cells. One of the advantages associated with using tumor cells is that tumor cells undergo relatively fast cell cycling or division, which may further enhance replication and amplification of the virus in the culture. The immortalized tumor cell lines can be generated from primary tumor cells or from established tumor cell lines. Alternatively, normal cells can also be used so long as the cells are immortalized. Examples include but are not limited to human transformed primary embryonal kidney 293 cells, primary cells immortalized by transfection with telomerase gene (Bodnar, A. G. et al. (1998) Science 279:349–352) and normal cells immortalized by SV40 tranformation. These immortalized cells can proliferate indefinitely, thus providing an ample and economic supply of cells.

Optionally, cell that expresses CD4 or a coreceptor (e.g. CXCR4 and CCR5) naturally, but at a low level, may also serve as the host cell according to the present invention. For example, HUT78 or CEM-NKr-R5 cells express CD4 and a low level of CXCR4 may be used for the production of the recombinant cells of the present invention.

b) Individual Vectors for the Reporter and Receptor Genes

In order to create a cell line which is permissive to HIV infection, CD4 and one or more other HIV receptors may be transfected, transduced or otherwise introduced into the immortalized host cells first. The one or more other HIV receptors preferably include CXCR4 and CCR5 receptors. The reporter gene for detecting HIV infection is then transferred into the host cells expressing CD4 and one or more HIV receptors.

CD4 receptor is believed to be the primary receptor for HIV entry into the host cell. It has recently been discovered that specific chemokine receptors such as CXCR4 and CCR5 receptors play important roles in mediating HIV entry and tropism for different target cells (reviewed by Berger, E. a. (1997) AIDS 11, Suppl. a: S3–S16; Dimitrov, D. S. (1997) Cell 91: 721–730). Macrophages-tropic (M-tropic) strains of HIV can replicate in primary CD4+ T cells and macrophages and use the beta-chemokine receptor CCR5 and less often, CCR3 receptor. T cell line-tropic (T-tropic) HIV strains can also replicate in primary CD4+ T cells but can in addition infect established CD4+ T cell lines in vitro via the alpha-chemokine receptor CXCR4. Many of the T-tropic strains can use CCR5 in addition to CXCR4. Chemokine receptor-like HIV coreceptor STRL33 is expressed in activated peripheral blood lymphocytes and T-cell lines and can function as an entry cofactor for Env proteins from M-tropic, T-tropic and dual tropic strains of HIV-1 and SIV. Other HIV coreceptors have also been identified by numerous in vitro assays, including chemokine receptors CCR2b, CCR3, CCR8 and CX3CR1 as well as several chemokine receptor-like orphan receptor proteins such as GPR15/BOB and STRL33/BONZO. Each or a set of these HIV coreceptors can mediate entry of different strains of HIV into the host cell. By transfecting, transducing or otherwise introducing these receptors into the immortalized cell line, the host cell line can be rendered permissive to HIV strains with broad-spectrum tropisms. In particular, by cell-cell fusion of the immortalized cell with cells expressing cell surface receptors known to be involved in HIV infection such as T-cells or monocytes, the immortalized cell can be transduced with various HIV receptors simultaneously.

By transfecting, transducing or otherwise introducing a selected set of coreceptors into an immortalized cell line or selectively expressing certain coreceptors on the cell surface, a cell line can be designed which is permissive to certain strains of HIV and is not be permissive to other strains of HIV. For example, CXCR4 coreceptor which is required by T-tropic strains can be selectively expressed in the recombinant cells to allow infection of T-tropic strains of HIV. Meanwhile, M-tropic strains require CCR5 coreceptor to infect cells. By having the recombinant cells not express CCR5 coreceptor, the recombinant cell line can selectively detect T-tropic strains in the presence of M-tropic strains.

In order to detect HIV infection with a high level of sensitivity, a "molecular switch" with high induction ratio is introduced into the immortalized cell line expressing CD4 receptor and the one or more additional HIV receptors. The molecular switch comprises a reporter gene whose expression is induced when the cells are infected by HIV. Various reporter genes can be used including lacZ (encoding β-galactosidase), luciferases gene, CAT gene, SEAP gene, and genes encoding fluorescent proteins such as green fluorescent protein (GFP), enhanced blue fluorescent protein (EBFP), enhanced yellow fluorescent protein (EYFP) and enhanced cyan fluorescent protein (ECFP).

The promoter region for the reporter gene contains a basic promoter and a single or multiple copies of HIV specific enhancer sequence. The basic promoter can be any cellular or viral basic promoters such as the basic promoter regions of β-actin promoter, insulin promoter, human cytomegalovirus (CMV) promoter, HIV-LTR (HIV-long terminal repeat), *Rous sarcoma* virus RSV-LTR, and simian virus SV40 promoter. The HIV specific enhancer sequence can be any sequence that can regulate the expression of the reporter gene via direct or indirect interaction with one or more HIV specific gene products. For example, the responsive element (TAR) for HIV transactivator protein Tat can be used to enhance the expression of the reporter gene. Upon infection of HIV, Tat expressed from the viral genome binds to TAR sequence and, coupled with the basic promoter, induces expression of the reporter gene. More than one copy of TAR sequence can be linked to further enhance expression of the reporter gene and raise the induction ratios.

Alternatively, expression of the reporter gene can be induced by protein-protein interactions between an HIV gene product, a DNA-binding protein (e.g. GAL4 DNA binding domain), a transactivator protein (e.g. VP16 transactivator domain derived from herpes simplex virus) that are expressed by the host cell. Upon binding of the HIV specific gene product to the DNA binding protein as well as to the transactivator protein, reconstitution of a transcription factor is achieved by bringing the DNA-binding protein and the transactivator protein into close approximately. The reconstituted transcription factor can then activate downstream reporter gene expression via the specific binding between the enhancer sequence (e.g. GAL4 enhancer sequence) upstream of the basic promoter with the DNA binding protein.

It should be noted that expression of a reporter gene can also be indirectly regulated by an HIV specific protein. For example, transcription of the reporter gene can be under the control a strong promoter, such as the bacteriophage T7 or SP6 promoters, while expression of T7 or SP6 polymerase is regulated by a promoter comprising a basic promoter and an HIV specific enhancer sequence. Upon binding of the HIV specific protein to the enhancer sequence, expression of T7 or SP6 polymerase is enhanced. As a result, T7 or SP6 polymerase expressed in the cell can then bind to the T7 or SP6 promoter upstream of the reporter gene and induce expression of the reporter gene in the cell.

Various methods can be used to introduce genes into the immortalized cells. Examples of methods that may be used include, but are not limited to, calcium phosphate-mediated direction transfection, liposome-assisted transfection, and virus-mediated transfection. HIV receptors can also be introduced into the host cell through cell fusion with natural cells expressing these receptors on the cell surface. Clones of cells expressing the transfected genes may be selected by antibiotics such as hygromyin, G418, zeocin, etc., or based on herpes simplex virus tk gene. Expression of each receptor gene may be confirmed by Western blot to detect the protein with an antibody, Northern blot to detect the RNA with a nucleotide probe, or by FACS using the HIV receptor expressed on the cell surface as antigens.

Two examples of plasmid vectors containing HIV receptor genes and a reporter gene are diagramed in FIGS. 1A and 1B.

As illustrated in FIG. 1A, CD4 and HIV co-receptors are expressed from SV40 early and late promoters in opposite directions. Genes encoding CD4 and CCR5 receptors are expressed from SV40 early promoter by a splicing mechanism at the SA sites. Genes encoding CXCR4 and hygromycin resistance are expressed bicistronically from SV40 late promoter with Hygro being separated by an internal ribosome entry site (IRES). Expression of hygromycin resistance gene enables selection of the cell. The plasmid also contains prokaryotic replication origin and ampicillin-resistance gene for DNA propagation in bacteria. The reporter gene is carried by a separate plasmid that contains a second selection gene (tk). The two plasmids may be co-transfected into HeLa cells simultaneously or sequentially. Cell clones expressing all of the transfected genes can be selected with antibiotics accordingly.

Genes encoding HIV receptor and coreceptors may also be expressed from the two retroviral vectors illustrated in FIG. 1B. The receptors gene are expressed from the murine leukemia virus (MLV) LTR-promoter, each protein is expressed from a spliced mRNA or from an IRES (B.1). The reporter sequence is carried by a second retroviral vector. Transcription of the reporter gene is in the opposite direction of the MLV LTR promoter with the enhancer sequence deleted in order to prevent unregulated expression from the LTR promoter (B.2).

These vectors are packaged into infectious but replication-incompetent virions by using a packaging cell line, such as those stable or transient production lines based on the 293T cell line. The packaging cell line expresses all the necessary proteins, Gag, Pol and Env, that are required for packaging, processing, reverse transcription, and integration of recombinant retroviral genome containing the Psi packaging signal.

The retroviral vectors are transfected into the packaging cell line. The virions produced in the packaging cells are then collected and used to infect a target cell. Since the virons are replication-incompetent, the genes carried by the retroviral vectors are stably integrated into the target cell genome and can be expressed under the control of the upstream promoter without producing infectious virions. The cells expressing all of the transduced genes can be selected with antibiotics and confirmed by Northern, Western blots or FACS accordingly. Alternatively, the cells expressing the reporter sequence can be selected by infecting the cell culture with a modified adenovirus carrying HIV specific gene such as tat.

It should be noted that expression of HIV receptors can also be controlled by an inducible promoter such as a tetracycline responsive element TRE. For example, one or more of the HIV coreceptors can be selectively presented on the cell surface by a controlled expression using the Tet-on and Tet-off expression systems provided by Clontech (Gossen, M. and Bujard, H. (1992) Proc. Natl. Acad. Sci. USA 89: 5547–5551). In the Tet-on system, gene expression is activated by the addition of a tetracycline derivative doxycycline (Dox), whereas in the Tet-off system, gene expression is turned on by the withdrawn of tetracyline (Tc) or Dox. Any other inducible mammalian gene expression systems may also be used. Examples include systems using heat shock factors, steroid hormones, heavy metal ions, phorbol ester and interferons to conditionally expressing genes in mammalian cells.

c) Recombinant Vector Systems for Constructing the Recombinant Cells

Recombinant vector system may also be used for transferring the reporter and receptor genes into the host cells to produce the recombinant cells according to the present invention. The vector may be a plasmid or a virus. The recombinant vector system may consist of a single vector or a plurality of recombinant vectors.

In one embodiment, a single recombinant plasmid is used to transfer the reporter and receptor genes into the host cell. The plasmid comprises: a reporter sequence comprising a reporter gene whose expression is regulated by a protein specific to HIV; and a receptor sequence comprising a CD4 gene and one or more coreceptor genes, the expression of the receptor and coreceptor genes facilitating productive infection of the transfected cell and enabling HIV which has infected the transfected cell to replicate and infect noninfected cells in a culture of the cells transfected with the recombinant plasmid.

Several non-viral methods can be used to transfer the recombinant plasmid into the host cells. Examples of non-viral methods include, but are not limited to calcium phosphate precipitation, electroporation, direct microinjection, DNA-loaded liposomes and lipofectamine-DNA complexes, cell sonication, gene bombardment using high velocity microprojectiles, and receptor-mediated transfection.

In a preferred embodiment, the single vector system is based on a recombinant virus, such as a modified or recombinant retrovirus, an adenovirus, an adeno-associated viruses, a vaccinia virus, Alpha virus, a VEE vector and a herpes simplex virus. The single viral vector system comprises: a reporter sequence comprising a reporter gene whose expression is regulated by a protein specific to HIV; and a receptor sequence comprising a CD4 gene and one or more coreceptor genes, the expression of the receptor and coreceptor genes facilitating productive infection of the transfected cell and enabling HIV which has infected the transduced cell to replicate and infect noninfected cells in a culture of the cells transduced by the recombinant virus.

Alternatively, a recombinant viral vector encoding the HIV receptor genes may be used to transduce cells that already contained the reporter sequence. The recombinant viral vector comprises: a CD4 gene and one or more coreceptor genes, the expression of the receptor and coreceptor genes facilitating productive infection of the transfected cell and enabling HIV which has infected the transduced cell to replicate and infect noninfected cells in a culture of the cells transduced by the recombinant virus.

The recombinant virus is preferably replication defective or replication incompetent. These viruses enter the host cells via receptor-mediated endocytosis, transfer foreign gene into the nucleus, and express the foreign and viral genes there. The transduction efficiency of a viral vector system is generally higher than the transfection efficiency of a non-viral vector system.

For retroviruses, the viral genome integrates into the host cell genome in a non-specific manner and expresses the foreign and viral genes stably and efficiently in transduced host cells. To construct a retroviral vector, a nucleic acid encoding the reporter and receptor genes is inserted into the viral genome in the place of certain viral sequences to produce a virus that is replication-defective. Virions containing the inserted gene are produced in a packaging cell line containing the gag, pol, and env genes but lacking the LTR and psi components. When a recombinant plasmid containing the inserted gene, together with the retroviral LTR and psi sequences is introduced into this cell line (by calcium phosphate precipitation, for example), the psi sequence allows the RNA transcript of the recombinant plasmid to be packaged into viral particles, which are then secreted into the culture media. The media containing the recombinant retrovirus is then collected, optionally concentrated, and used for transferring the reporter and receptor genes into the host cell to produce the recombinant cells of the present invention.

In more preferred embodiment, the single vector system is a recombinant adenoviral vector that is replication incompetent. Compared to retroviruses, one of the advantages of an adenoviral vector is that infection of adenoviral DNA into host cells does not result in chromosomal integration because adenoviral DNA can replicate in an episomal manner without potential genotoxicity. Also, adenovirus is structurally stable, and no genome rearrangement has been detected after extensive amplification. Adenoviral vectors can infect a variety of cells regardless of their cell cycle stage. Adenoviral vectors have been safely used in gene therapy trials in which patients have tolerated $10^{13}$ infectious particles instilled into the lungs. A replication defective adenoviral virus that is dried into powder can be transported and stored safely for an extended period time without losing its infectability.

Adenovirus is particularly suitable for use as a gene transfer vector because of its mid-sized genome, ease of manipulation, high titer, wide target cell-range, and high infectivity. Both ends of the viral genome contain 100–200 base pair inverted terminal repeats (ITL), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off. The products of the late genes, including the majority of the viral capsid proteins, are expressed only after significant processing of a single primary transcript issued by the major late promoter (MLP). The MLP is particularly efficient during the late phase of infection, and all the mRNAs issued form this promoter possess a 5' tripartite leader (TL) sequence which makes them preferred mRNA for translation.

Generation and propagation of a replication incompetent adenoviral vector is carried out in a helper cell line. A helper cell line expresses the essential genes, such as E1, E2, E4 or late genes, which have been deleted from the viral vector. Helper cell lines may be derived from human cells such as human embryonic kidney cells (e.g. 293 cells), muscle cells, hematopoietic cells or other human embryonic mesenchymal or epithelial cells. Altenatively, the helper cells may be derived from the cells of other mammalian species that are permissive for human adenovirus. Such cells include, e.g. Vero cells or other monkey embryonic mesenchymal or epithelial cells.

The recombinant adenoviral vector may be derived from any of the serotypes or subgroups A–F. Adenovirus type 5 of group C may be the preferred starting material in order to obtain the replication incompetent adenoviral vector for constructing the recombinant cells of the present invention. This is because adenovirus type 5 is a human adenovirus about which a great deal of biochemical and genetic information is known, and it has historically been used for most constructions employing adenovirus as a vector.

In one embodiment, the recombinant adenoviral vector comprises: a reporter sequence comprising a reporter gene whose expression is regulated by a protein specific to HIV; and a receptor sequence comprising a CD4 gene and one or more coreceptor genes, expression of the receptor and coreceptor genes facilitating productive infection of the transduced cell and enabling HIV which has infected the transduced cell to replicate and infect noninfected cells in a culture of the cells transduced by the recombinant adenoviral vector.

The genes encoding the HIV receptors may be placed under transcriptional control of a constitutive (e.g. CMV and SV40) or an inducible (e.g. tetracycline-inducible) promoter located in the E1 region of the adenoviral vector near the left terminal repeats (L-TR). The reporter sequence may be positioned in the right end of the recombinant adenoviral vector, for example, in the E4 region of the recombinant adenoviral vector near the right terminal repeats (R-TR).

In another embodiment, the recombinant adenoviral vector comprises: a CD4 gene and one or more coreceptor genes, expression of the receptor and coreceptor genes facilitating productive infection of the transduced cell and enabling HIV which has infected the transduced cell to replicate and infect non-infected cells in a culture of the cells transduced by the recombinant adenoviral vector.

For example genes encoding HIV coreceptors CCR5 and CXCR4 may be placed under transcriptional control of a constitutive (e.g. CMV and SV40) or an inducible (e.g. tetracycline-inducible) promoter located in the E1 region of the adenoviral vector near the left terminal repeats (L-TR). CCR5 and CXCR4 can be expressed bicistronically under the transcriptional control of a heterologous promoter (e.g., a $CMV_{ie}$ promoter) by a splicing mechanism at the SA sites and via an internal ribosome entry site (IRES). Genes encoding CD4 and/or CXCR4 may be positioned in the right end of the recombinant adenoviral vector, for example, in the E4 region of the recombinant adenoviral vector near the right terminal repeats (R-TR).

The recombinant adenoviral vector may be replication incompetent but carry an adenoviral packaging signal. The adenoviral vector carries genes encoding HIV receptors, such as CD4, CXCR4 and CCR5, as well as a reporter gene such as β-galactosidase, luciferase, beta-glucuronidase, chloramphenicol acetyl transferase (CAT), fluorescent protein (e.g. GFP and BFP), secreted embryonic alkaline phosphatase (SEAP), hormones and cytokines. The vector may also carry a gene encoding an interleukin (e.g. IL-2 and IL-12) that renders the transduced cells more susceptible to HIV infection. The vector may also carry a eukaryotic polyadenylation sequence such a SV40 polyadenylation site or a bovine growth hormone (BGH) polyadenylation site.

It should be noted that various HIV receptors may be transferred into the cells by a single recombinant viral vector carrying all of the HIV receptors as described above. Alternatively, the receptor genes may be carried by multiple recombinant viral vectors, each containing one or more HIV receptors to confer upon the cell different tropisms.

The present invention also provides a kit for producing the recombinant cells described above. In one embodiment, the kit comprises: a recombinant viral vector and a cell line capable of being infected by the vector, the recombinant viral vector comprising a reporter sequence comprising a reporter gene whose expression is regulated by a protein specific to HIV, and a receptor sequence comprising a CD4 gene and one or more coreceptor genes, expression of the receptor and coreceptor genes facilitating productive infection of the transduced cell and enabling HIV which has infected the transduced cell to replicate and infect noninfected cells in a culture of the cells transduced by the recombinant viral vector.

In another embodiment, the kit comprises: a recombinant viral vector and a cell line capable of being infected by the vector, the recombinant viral vector comprising a CD4 gene and one or more coreceptor genes and the cell line containing a reporter gene whose expression is regulated by a protein specific to HIV, expression of the receptor and coreceptor genes facilitating productive infection of the transduced cell and enabling HIV which has infected the transduced cell to replicate and infect noninfected cells in a culture of the cells transduced by the recombinant viral vector.

The present invention also provides a method for producing recombinant cells for detecting a presence of HIV in a sample. In one embodiment, the method comprises: taking a culture of cells; and adding a recombinant viral vector into the culture to transduce the cells, the recombinant viral vector comprising a reporter sequence comprising a reporter gene whose expression is regulated by a protein specific to HIV, and a receptor sequence comprising a CD4 gene and one or more coreceptor genes, expression of the receptor and coreceptor genes facilitating productive infection of the transduced cell and enabling HIV which has infected the transduced cell to replicate and infect noninfected cells in the culture of the cells transduced by the recombinant viral vector.

In another embodiment, the method comprises: taking a culture of cells that contains a reporter sequence comprising a reporter gene whose expression is regulated by a protein specific to HIV; and adding a recombinant viral vector into the culture to transduce the cells, the recombinant viral vector comprising a CD4 gene and one or more coreceptor genes, expression of the receptor and coreceptor genes facilitating productive infection of the transduced cell and enabling HIV which has infected the transduced cell to replicate and infect noninfected cells in the culture of the cells transduced by the recombinant viral vector.

Alternatively, the recombinant cells of the present invention may be produced by transducing cells that already express CD4 and one or more HIV coreceptors such as CXCR4 and CCR5 with a recombinant viral vector containing the reporter sequence. The CD4 and one or more HIV coreceptors may be expressed at levels sufficient for facilitating productive infection of the cells by HIV.

Optionally, the recombinant cells of the present invention may also be produced by transducing cells that already contains the reporter sequence with a recombinant viral vector that expresses CD4 and one or more HIV coreceptors. Upon infection of HIV, expression of the reporter gene on the reporter sequence is activated by a protein specific to HIV (e.g. Tat).

The recombinant cells of the present invention may also be produced by transducing cells that already contains the reporter sequence and CD4 or at least one HIV coreceptor with a recombinant viral vector that expresses CD4 or at least one HIV coreceptor at sufficient levels to facilitate productive infection of HIV in the cells. Upon infection of HIV, expression of the reporter gene on the reporter sequence is activated by a protein specific to HIV (e.g. Tat).

The recombinant viral vector of the present invention may also be used to transduce a cell that expresses CD4 or a coreceptor (e.g. CXCR4 and CCR5) naturally, but at a low level. For example, HUT78 and CEM-NKr-R5 cells express CD4 and a low level of CXCR4. Such cells may be transduced by the recombinant viral vector that contains CD4 or the other coreceptors necessary for productive HIV infection of cells in the culture. Alternatively, the cell may be transfected by a recombinant plasmid according the embodiment described above. By introducing a vector carrying the HIV receptor into the cell, the expression levels of the HIV can be significantly elevated by using strong promoters (such as CMV and SV40 promoters) to overexpress the receptors.

The recombinant viral vector of the present invention may also be used produce cells that express the receptors in a controlled period of time by using an inducible promoter, or in a shorter period of time by using an adenoviral vector. This allows versatile and efficient production of a wide variety of cells which can be used for detecting HIV infection in the cell, screening for anti-HIV drugs and detecting HIV drug resistance in the cells.

Overall, the present invention provides novel recombinant vectors and cell lines, and methods using these cell lines. These methods are convenient, cost-effective and ultra sensitive for the detection of HIV infection and replication. These methods can be very useful for high throughput screening in drug and vaccine discovery and development, as well as designing more efficacious anti-HIV drug cocktails in the clinic to combat HIV drug resistance.

EXAMPLE

1. Productive Infection of Recombinant HeLa Cells with HIV

Figure 2:
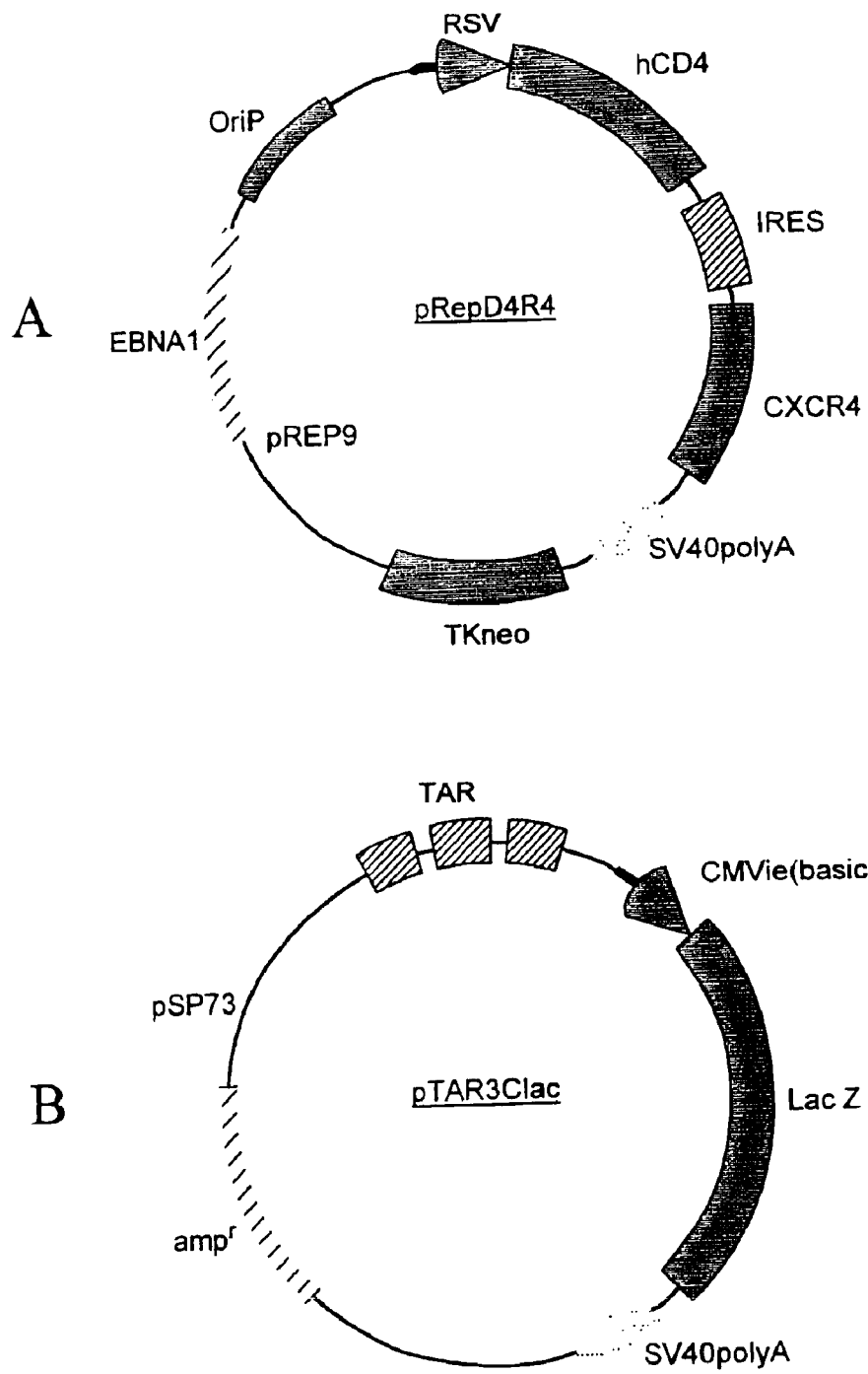
FIG. 2A illustrates an expression plasmid for human CD4 and CXCR4 receptors.
FIG. 2B illustrates a plasmid for a lacZ reporter gene.

A recombinant cell line was established from human cervical cancer HeLa cells. The HeLa cells were cotransfected with an expression vector (pRepD4R4) and a vector (pTAR3Clac) at a 1:1 ratio. As shown in FIG. 2A the expression vector pRepD4R4 includes CD4 receptor and CXCR4 receptor genes that are separated by an IRES sequence. As shown FIG. 2B the vector pTAR3Clac includes a reporter sequence comprising a promoter region that includes three copies of TAR sequences and a CMV basic promoter, and a lacZ reporter gene whose expression is under the control of the promoter. The stably-transfected cells were selected by culturing in medium containing G418 at 900 μg/ml. Each clone of the cells selected was subsequently cultured in duplicates, and one of the duplicates was infected with a low titer HIV stock solution. The low-titer HIV stock was collected from supernatant of a HeLa cell culture that was transfected with a B-cell tropic HIV provirus DNA (strain GRCSF) and incubated for 3 days post transfection.

Upon infection of HIV contained in the stock solution, Tat protein expressed from the viral genome binds to TAR and induces expression of lacZ reporter gene to produce high level of β-galactosidase. The cell clones expressing β-galactosidase and stained blue with X-gal were identified, and the cells from the uninfected duplicate of the darkest blue colony were propagated. Such selected cells were designated as HeLaD4R4 cells.

HeLaD4R4 cells constructed as described above were tested for HIV infection. HeLaT4 cells (also called HT4) which express human CD4 receptor were used as a control. The HeLaD4R4 cells and HeLaT4 cells were grown up in DMEM and 5% bovine calf serum.

Exponentially growing cells were cultured in a six-well plate and infected with 1 ml of a diluted HIV stock (about 10 infectious particles (i.p.)/ml) obtained from HIV provirus transfected HeLa cell culture as described above. The cells were continuously cultured, and fixed with 1% formaldehyde for 2 minutes 1, 3, 4, 5 days after the initial infection. The cells were fixed with 0.5% formaldehyde for 2 min. and stained with X-gal (0.5%) at 37° C. over night. Since the lacZ reporter gene product, β-galactosidase, converts the substrate from colorless to dark blue, cells expressing β-galactosidase as a result of being infected with HIV appear distinctly blue.

FIG. 3A shows the control HeLaT4 cells after three days of being exposed to HIV. As can be seen, almost all of the HeLa cells were not stained blue, with few cell stained faint blue. This indicates that cells without HIV CXCR4 were poorly infected and the HIV did not replicate within the cell culture.

FIGS. 3B–2E shows HeLaD4R4 after 1, 3, 4, and 5 days. As can be seen in FIG. 3B, infection can be readily detected after 1 day, as shown by the blue cells. As can be seen in FIGS. 3C and 3D respectively, progressively more cells were infected and stained blue after 3 and 4 days. As can be seen in FIG. 3E, virtually all cells in the well were infected and stained dark blue after 5 days.

The results shown in FIGS. 3B–3E indicate that following initial infection of a few cells by about ten HIV virions, HIV was able to undergo a productive infection, i.e. an infection of a cell which is fully permissive for virus replication and production of progeny virions (Stevenson, M. AIDS 11 Suppl. a: S25–S33). In addition, the infected cells appear to retain normal morphology, i.e. remaining attached to the substrate of the culture plate instead of rounding up and detaching from the plate.

The results shown in FIG. 3E are particularly significant because HIV virions initially added to the sample were able to replicate within the cell culture and spread to infect other cells that are not infected originally (compare FIGS. 3B and 3E). This is in significant contrast to an increase of cells stained blue simply due to cell division.

FIG. 3F illustrates a further experiment where AZT (100 μg/ml) was added to inhibit HIV replication and infection. As can be seen in FIG. 3F, after four days of incubation in the presence of AZT only a few clusters of cells were infected and stained blue. The sparse clusters of blue cells are most likely cells divided from the few cells that were initially infected by the HIV virions added to the well.

Figure 3:
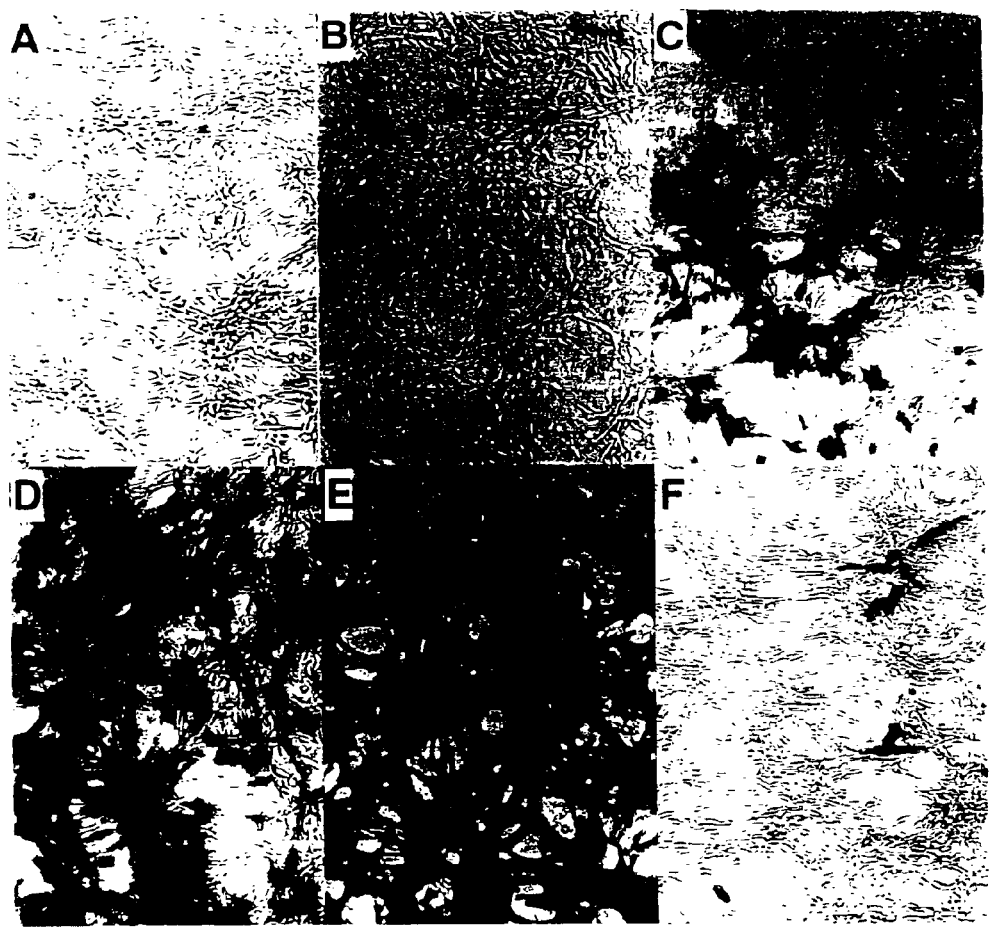
FIG. 3A shows HeLaT4 cells cultured in the presence of HIV and later processed with X-Gal.
FIG. 3B shows HeLa D4R4 cells cultured in the presence of HIV and later processed with X-Gal 1 day after the initial infection.
FIG. 3C shows HeLa D4R4 cells cultured in the presence of HIV and later processed with X-Gal 3 days after the initial infection.
FIG. 3D shows HeLa D4R4 cells cultured in the presence of HIV and later processed with X-Gal 4 days after the initial infection.
FIG. 3E shows HeLa D4R4 cells cultured in the presence of HIV and later processed with X-Gal 5 days after the initial infection.
FIG. 3F shows HeLa D4R4 cells cultured in the presence of HIV and AZT and later processed with X-Gal.

By comparing FIG. 2F to FIGS. 3B–3E, one can see that AZT was effective as an anti-HIV agent since the expression of the reporter gene was significantly reduced due to the presence of AZT. This comparison of the results in FIG. 3F to FIGS. 3B–3E is an example of how the present invention can be used to detect HIV drug resistance and to screen compositions for anti-HIV activity.

2. Method for HIV Diagnosis

An example is provided for detecting HIV in a sample. This method can be used to diagnose a patient infected with HIV. According to the method, recombinant cells are seeded into a multiple well plate. a small amount of serum from an individual to be tested is added to duplicates of the wells. After two to four days incubation, the cells are processed and the results are analyzed depending on the type of reporter gene used. For example, when lacZ gene is used as the reporter gene for the recombinant cells, the cells are treated with a processing solution containing the substrate X-Gal for β-galactosidase, low concentration of formaldehyde (1%) and glutaraldehyde the (0.1%) to gently fix the cells while not inactivating the reporter protein. When a green fluorescent protein (GFP) gene is as the reporter gene for the recombinant cells, the cells are observed under an UV microscope directly. The presence of cells emitting green fluorescence indicate that the cells may have been infected by HIV contained in the sample. By using GFP as a reporter gene replication of HIV can be directed monitored any time during the incubation without fixing and processing cells to ensure that enough HIV has been replicated within the culture.

The above-described diagnosis test can be used as an independent test for HIV infected patients, or in conjunction with HIV drug resistance and other HIV diagnosis tests.

A positive control agent may be used to ensure that the recombinant cells are responsive to HIV infection. A defective common cold virus strain carrying an HIV tat gene that encodes HIV transactivator protein Tat may be used as a positive control agent. The common cold virus is used as a vector to transfer the HIV tat gene into cells to mimic HIV infection. HIV itself may not be ideal for use as a positive control because HIV may not be sufficient stable and can easily lose its activity, thus the virus may not be stored for an extended period of time. In contrast, the common cold virus can be dried into powder and stored for a long time. In addition, this strain of common cold virus is derived from a strain of common cold virus (adenovirus type 5) that is defective in viral replication, therefore safer for an extensive usage as a positive control.

3. Method for Detecting HIV Drug Resistance

An example of how to perform the method for detecting HIV drug resistance is provided. Recombinant cells are seeded into each well of a multiple-well plate. Duplicate wells contain each anti-HIV agent to be tested. A small amount of patient serum is added to each well and incubated for a few days. After two to four days of incubation, the cells are processed and the results are analyzed depending on the type of reporter gene used. For example, when lacZ gene is used as the reporter gene for the recombinant cells, the cells are treated with a processing solution containing the substrate X-Gal for β-galactosidase, low concentration of formaldehyde (1%) and glutaraldehyde the (0.1%) to gently fix the cells while not inactivating the reporter protein. For quantitative analysis, levels of β-Gal can be measured by an ONPG assay on the cell extract. When a green fluorescent protein (GFP) gene is used as the reporter gene for the recombinant cells, the cells are observed under an UV microscope directly. For quantitative analysis, the fluorescent cells are sorted by FACS and numbers of cells expressing the GFP reporter are measured.

If the cells in the wells containing a particular drug express the reporter gene at a sufficient level, it indicates that the HIV contained in the sample may be resistant to the drug at the tested dose, and the virus has replicated and spread the infection among the recombinant cells in the presence of the anti-HIV drug.

Wells where no serum sample has been added can be used as a negative control. Negative controls can be performed for each agent being tested. A positive control, for example using the positive control agent described in Example 2 (adenovirus carrying HIV tat gene), can also be performed for each agent tested to ensure that the recombinant cells function properly.

4. Method for Determining Viral Load in a Patient Serum

An example of how to perform the method for determining viral load in patient serum is provided. About 1 milliliter of patient☐s serum is diluted progressively, such as 1:10, 1:100, 1:1000, etc, and added to wells containing the recombinant cells. The highest dilution that still induces expression of the reporter gene of the recombinant cells in the well is the titer (concentration) of the HIV in the patient serum. When the viral load become low, finer steps of dilution may be performed to determine more accurately the numbers of viral particles in the patient's serum.

The method can be used to determine how many viral particles per milliliter are present in patient serum. Since the recombinant cells in a culture are sensitive to infection of even a single virion, this method can detect infection by only one viral particle, therefore suitable for detecting a patient sample containing low titer HIV, even a few viral particles per milliliter of patient serum. Such a high sensitivity is important for monitoring the progress of anti-HIV drug treatment. Compared to the "ultra-sensitive" PCR-based assays that can only detect hundreds or more viral particles per milliliter of patient serum, this method is more sensitive and can be used to detect much lower titer HIV in the sample. This is particularly important for detecting HIV in a patient sample after anti-HIV drug treatment when viral titer is below the detectable level of conventional HIV detection methods.

5. Method for Screening for Anti-HIV Agents

Described here is an example of a method for performing high throughput anti-HIV drug screening. To screen for new anti-HIV agents, the recombinant cells are seeded into a multiple well plate, such as 96-well plate. To each well the agent to be tested for anti-HIV activity is added. a small amount of HIV stock is added to each well, so that the cells in each well are infected with about 10 viral particles. After a few days of incubation, the cells in the wells are analyzed on a calorimetric or fluorescence plate reader. The wells are compared with one or more wells containing the recombinant cell and virus but not the agent. Inhibition of the expression of the reporter gene in wells containing an agent indicates that the agent may have anti-HIV activity at the tested dose. Once potential anti-HIV agents have been identified, the test may be repeated to further confirm the anti-HIV activity of the agent.

6. Construction of Recombinant Adenoviral Vector

A recombinant adenoviral vector of the present invention is constructed by using shuttle plasmids or vectors carrying the receptor sequence and the reporter sequence.

1) Construction of rAd-R5-D4-X4/Repo Vector

Figure 4A:
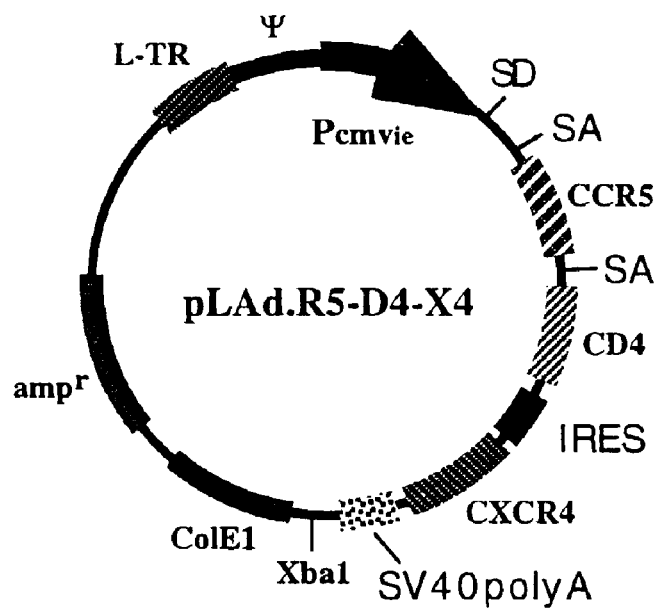
FIG. 4A illustrates a shuttle plasmid for human CD4, CXCR4 and CCR5 receptors.

FIG. 4A illustrates a shuttle plasmid (pLAd.R5-D4-X4) containing human CD4, CXCR4 and CCR5. The shuttle plasmid pLAd.R5-D4-X4 contains the left end of the adenoviral genome including the left long terminal repeats L-TR, and an adenoviral packaging signal (ψ). The E1 region of the adenovirus is replaced by a multiple gene expression cassette and $CMV_{ie}$ promoter.

Genes encoding CD4, CXCR4 and CCR5 are placed under the transcriptional control of the $CMV_{ie}$ promoter by a splicing mechanism at the SA sites and by an internal ribosome entry site (IRES). The plasmid pLAd.R5-D4-X4 also contains a SV40 polyadenylation site, as well as prokaryotic replication origin and ampicillin-resistance gene for DNA propagation in bacteria.

Figure 4B:
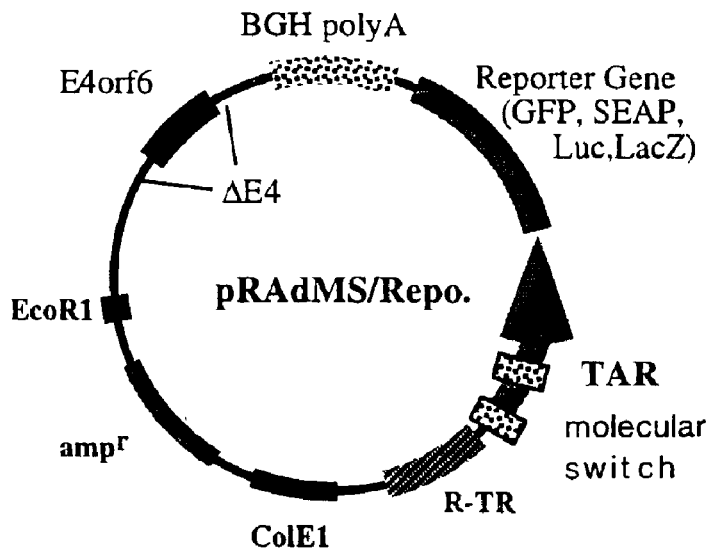
FIG. 4B illustrates a shuttle plasmid for a reporter gene.

FIG. 4B illustrates another shuttle plasmid (pRAdMS/Repo) containing a reporter sequence. The shuttle plasmid pRAdMS/Repo contains the right end of the adenoviral genome including the right long terminal repeats R-TR. Most of the E4 region (except orf6) is replaced by the reporter sequence including a HIV TAR-containing promoter and a reporter gene such as GFP, SEAP, Luc, and LacZ. Expression of the reporter gene can be activated by Tat protein of HIV. The plasmid pRAdMS/Repo also contains a bovine growth hormone (BGH) polyadenylation site, as well as a prokaryotic replication origin and ampicillin-resistance gene for DNA propagation in bacteria.

The recombinant adenoviral genome is assembled from the two shuttle plasmids, pLAd.R5-D4-X4 and pRAdMS/Repo, which carries the left and right end of the adenoviral genome, respectively. The shuttle plasmids pLAd.R5-D4-X4 and pRAdMS/Repo are digested with restriction enzymes such as Xbal and EcoRI, respectively.

Figure 6:
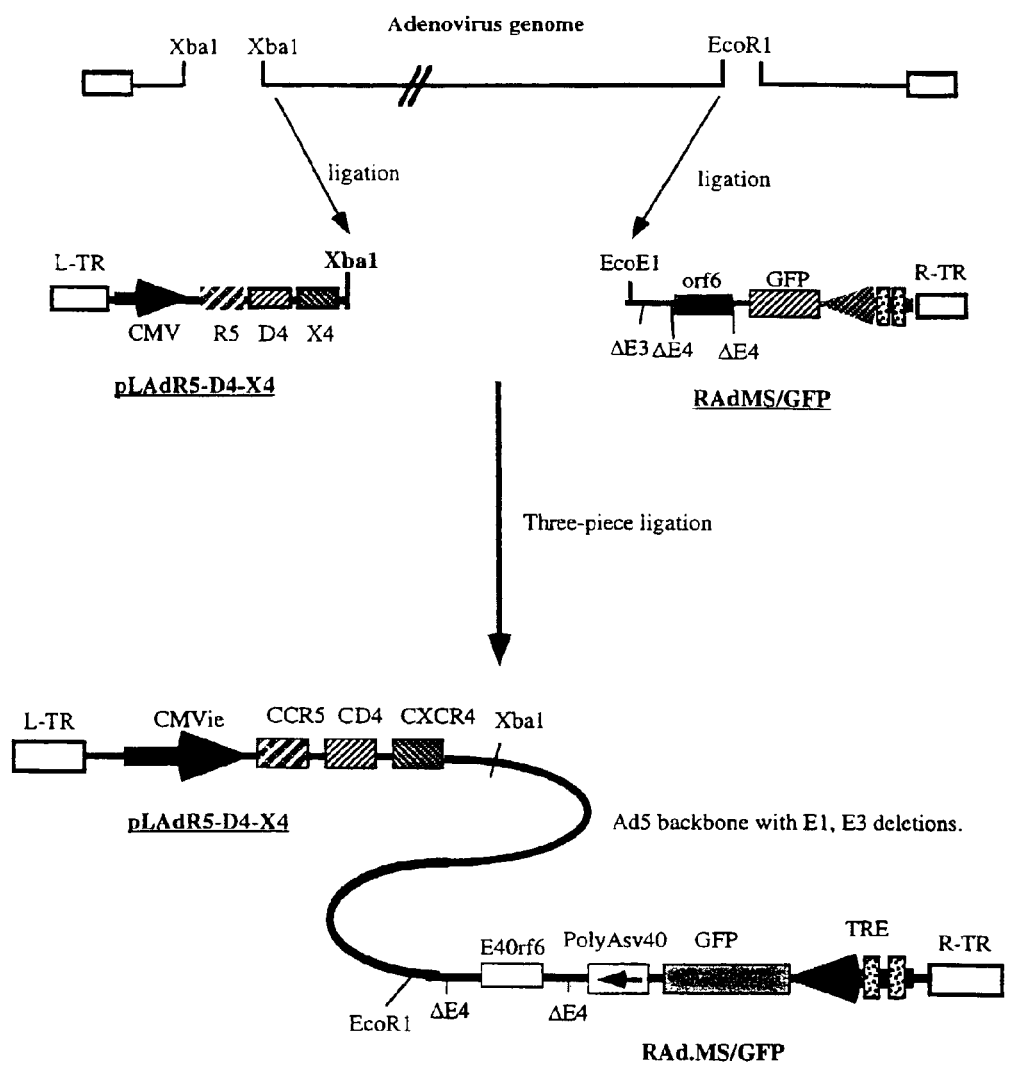
FIG. 6 illustrates a scheme for construction of a recombinant adenoviral vector of the present invention.

As illustrated in FIG. 6, the fragments corresponding to the left end and right end of adenovirus from these two shuttle plasmids, pLAd.R5-D4-X4 and pRAdMS/Repo, are isolated and ligated to the middle section of the adenoviral genome (the adenovirus backbone).

The ligated vector genome DNA is then transfected into 293HK cells that express the E1 proteins of adenovirus. In the presence of E1 proteins, the vector genome in which the E1 has been deleted can replicate and be packaged into viral particle, i.e. producing the recombinant adenoviral vector rAd-R5-D4-X4/Repo.

2) Construction of rAd-R5-X4-D4 Vector

Figure 5A:
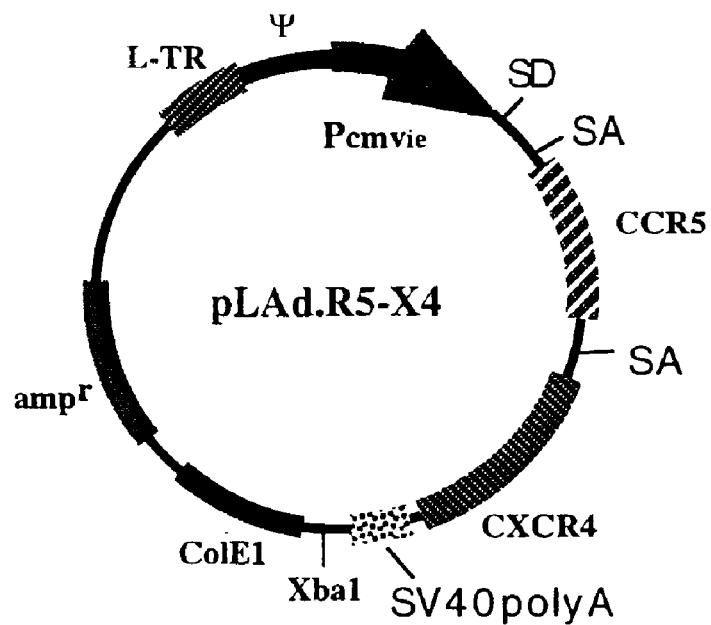
FIG. 5A illustrates a shuttle plamsid for human CXCR4 and CCR5 receptors.
Figure 5B:
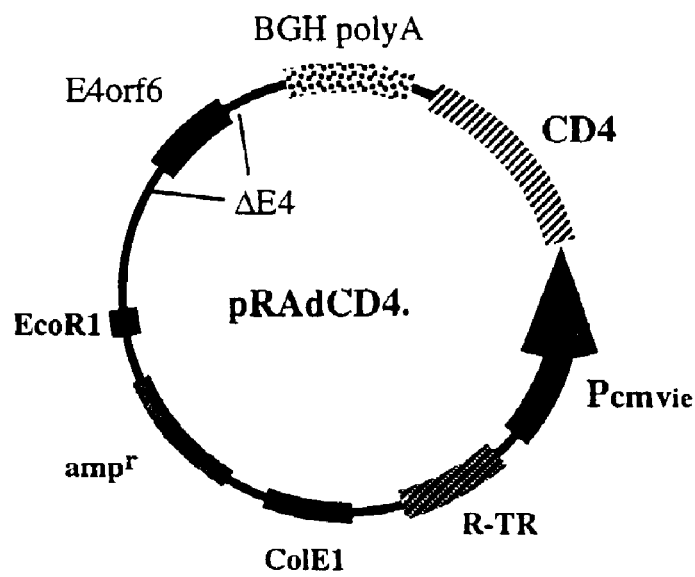
FIG. 5B illustrates a shuttle plamsid for human CD4 receptor.

FIGS. 5A and 5B illustrate an alternative design for constructing a recombinant adenoviral vector. As illustrated in FIG. 5A, the shuttle plasmid pLAd.R5-X4 carries human CXCR4 and CCR5. The shuttle plasmid pLAd.R5-X4 contains the left end of the adenoviral genome including the left long terminal repeats L-TR, and an adenoviral packaging signal (ψ). The E1 region of the adenovirus is replaced by a multiple gene expression cassette and $CMV_{ie}$ promoter. Genes encoding CXCR4 and CCR5 are placed under the transcriptional control of the $CMV_{ie}$ promoter by a splicing mechanism at the SA sites. The plasmid pLAd.R5-X4 also contains a SV40 polyadenylation site, as well as a prokaryotic replication origin and ampicillin-resistance gene for DNA propagation in bacteria.

FIG. 5B illustrates a shuttle plasmid (pRAdCD4) containing human CD4 gene. The shuttle plasmid pRAdCD4 contains the right end of the adenoviral genome including the right long terminal repeats R-TR. Expression of CD4 is under the control of the $CMV_{ie}$ promoter. The plasmid pRAdCD4 also contains a BGH polyadenylation site, as well as prokaryotic replication origin and ampicillin-resistance gene for DNA propagation in bacteria. The genes encoding the human HIV receptors such as CD4, CXCR4 and CCR5 may be interchangeable between these two plasmids, pRAdCD4 and pLAd.R5-X4. In this alternative design, the recombinant adenoviral vector only carries the receptor and coreceptor genes. This vector can be used in combination with a recombinant cell line that contains a reporter gene controlled by the HIV-protein (e.g., Tat) inducible promoter (e.g., TAR). Conversely, the vector carrying the reporter gene may be used in combination with a natural or recombinant cell line that contains genes encoding HIV receptor (CD4) and coreceptor (e.g., CXCR4 and CCR5).

Following a strategy similar to that shown in FIG. 6, the two shuttle plasmids, pLAd.R5-X4 and pRAdCD4, are subjected to restriction digestion and the restriction fragments are isolated and ligated to the middle section of the adenoviral genome (the adenovirus backbone).

The ligated vector genome DNA is then transfected into 293HK cells that express the E1 proteins of adenovirus. In the presence of E1 proteins, the vector genome in which the E1 has been deleted can replicate and be packaged into viral particle, i.e. producing the recombinant adenoviral vector rAd-R5-X4-D4.

3) Construction of rAd-R5-X4-D4-X4 Vector

Figure 7A:
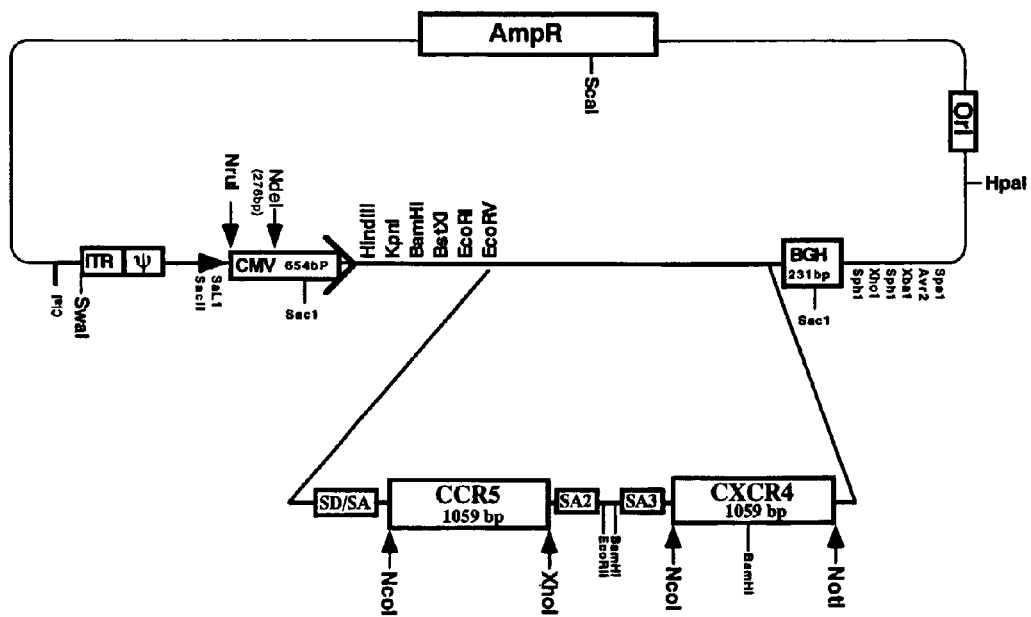
FIG. 7A illustrates a shuttle plasmid pLAd.R5-X4 encoding human CCR5 and CXCR4.
Figure 7B:
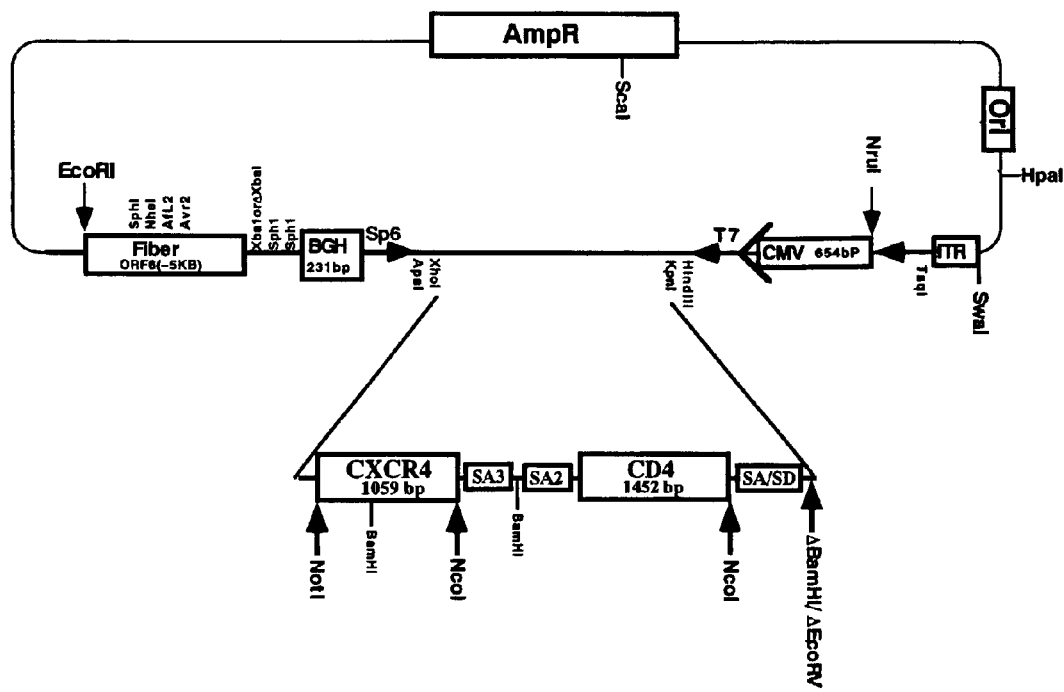
FIG. 7B illustrates a shuttle plasmid pRAd.CMV.Fiber.ORF-CD4.CXCR4 encoding human CD4 and CXCR4.

FIGS. 7A and 7B illustrate another alternative design for constructing a recombinant adenoviral vector. As illustrated in FIG. 7A, the shuttle plasmid pLAd.R5-X4 carries human CCR5 and The shuttle plasmid pLAd-CCR5.CXCR4 contains the left end of the adenoviral genome including the left long terminal repeats L-TR, and an adenoviral packaging signal ($\psi$). The E1 region of the adenovirus is replaced by a multiple gene expression cassette and $CMV_{ie}$ promoter. Genes encoding CCR5 and CXCR4 are placed under the transcriptional control of the $CMV_{ie}$ promoter by a splicing mechanism at the SD and SA sites. This plasmid also contains a bovine growth hormone (BGH) polyadenylation site, as well as a prokaryotic replication origin and ampicillin-resistance gene for DNA propagation in bacteria.

FIG. 7B illustrates a shuttle plasmid (pRAd.CMV.Fiber.ORF-CD4.CXCR4) containing human CD4 and CXCR4 genes. This shuttle plasmid contains the right end of the adenoviral genome including the right long terminal repeats R-TR. Most of the E4 region (except orf6) is replaced by the human CD4 and CXCR4 genes. CD4 and CXCR4 are expressed biscistronically under the transcriptional control of the $CMV_{ie}$ promoter via an internal ribosomal entry site (IRES) and by a splicing mechanism at the SD and SA sites. The plasmid pRAdCD4 also contains a BGH polyadenylation site, as well as prokaryotic replication origin and ampicillin-resistance gene for DNA propagation in bacteria.

Following a strategy similar to that shown in FIG. 6, the two shuttle plasmids, pLAd.R5-X4 and pRAdCD4, are subjected to restriction digestion and the restriction fragments are isolated and ligated to the middle section of the adenoviral genome (the adenovirus backbone).

The ligated vector genome DNA is then transfected into 293HK cells that express the E1 proteins of adenovirus. In the presence of E1 proteins, the vector genome in which the E1 has been deleted can replicate and be packaged into viral particle, i.e. producing the recombinant adenoviral vector rAd-R5-X4-D4-X4.

The recombinant adenoviral vectors of the present invention can be preserved as lyophilized powder for long term storage and shipment. The recombinant adenoviral vector can be used for detecting the presence of HIV in a clinical sample, for high throughput anti-HIV drug screening, and for monitoring HIV drug-resistance.

6. Expression Levels of HIV Receptors Encoded by a Complex Adenoviral Vector

The levels of HIV receptors, CD4, CXCR4 and CCR5 expressed from the complex adenoviral vector rAd-R5-X4-D4-X4 in transduced HeLa cells were measured by using a fluorescence activated cell sorter (FACS). Before the transduction of the complex adenoviral vector, the HeLa cells already contained a GFP reporter gene under the transcriptional control of a molecular switch composed of 2 copies of TAR.

The HeLa cells were analyzed after 48 hours of transduction of rAd-R5-X4-D4-X4 vector. Briefly, $1 \times 10^5$ cells mixed with $2 \times 10^6$ rAd-R5-X4-D4-X4 at m.o.i. 20 were applied in each 6-well plate. At day 2 (after 48 hours infection), the cells were removed by 10 mM EDTA in PBS, and washed with PBS containing 5% cosmic calf serum (CCS). The cells were blocked with 2% BSA+4% milk in PBS for 20 min. at room temperature. Then the cells incubated for 30 to 45 min at room temperature with each individual antibody, the phycoerythrin-labeled anti-CXCR4 MAb (Pharmingen Inc., San Diego, Calif.), the isothiocyanate-labeled anti-CCR5 Mab (Pharmingen Inc., San Diego, Calif.), the FICA-labeled anti-CD4 (Pharmingen Inc., San Diego, Calif.). After incubation with antibodies, the cells were washed three times with PBS+5% CCS and resuspended in 50 $\mu$l of PBS+5% CCS for FACS analysis. FIGS. 8A–C are FACS graphs showing the levels of the HIV receptors, CD4, CXCR4 and CCR5, respectively, expressed on the surface of the HeLa cells transduced with the adenoviral vector. FIGS. 8D–F show photographs of those cells stained with fluorescence-labeled antibodies against CD4, CXCR4 and CCR5, respectively.

FIG. 8G shows a table summarizing FACS analysis of expression levels of CD4, CXCR4 and CCR5 in HeLa cells transduced with rAd-R5-X4-D4-X4 at different m.o.i. levels, and those of the indicator cell lines developed by others: HUT78 (Gazdar et al. (1980) Blood 55:409–417), CEM-NKR-R5 (Howell et al. (1985) J. Immunol. 134:971–976; and Trkola et al. (1999) J. Virol. 73:8966–8974), Molt-4-R5 (Baba et al. (2000) AIDS Res. Hum. Retroviruses 16:935–941), CEM-A (Tremblay et al. (1989) J. Med. Virol. 28:243–249), and MAGI cell lines Chackerian et al. (1997) J. Virol. 71 :7719–7727; Kimpton and Emerman (1992)J. Virol. 66:3026–3031; and Vodicka et al. (1997) Virology 233:193–198).

HeLa cells were transduced with rAd-R5-X4-D4-X4 (Indicator #44) at m.o.i. 30 and 60, after 48 hr of infection removed from tissue culture by were removed from tissue culture dish by 10 mM EDTA in PBS+10% CCS, and then washed twice with PBS+10% CCS. Anti-HIV receptor antibodies labeled with single-color fluorescence (CD4-PE, CXCR4-PE, and CCR5-PE) were incubated with these cells at about $5 \times 10^6$ cells/sample for about 60 mm. in PBS+10% CCS+2% BSA. Then the cells were washed twice with PBS+10% CCS. Finally, the cells were resuspended in 200 $\mu$l of PBS+10% CCS for FACS analysis. MAGI cells were subjected FACS analysis following the same protocol as that for Indicator #44 cells. Suspension cells such as HUT78, CEM-NKR-R5, Molt-4-R5, and CEM-A cells were directly washed with PBS+10% CCS, incubated with antibodies against CD4, CXCR4 and CCR5, and subjected to FACS analysis.

As listed in a column labeled "Mb 1Mean" in the table shown in FIG. 8G, HeLa cells transduced with rAd-R5-X4-D4-X4 (Indicator #44) expressed much higher levels of CD4, CXCR4, CCR5 than those of indicator cells developed by others. Significantly, the expression levels of both CXCR4 and CCR5 are almost 10 times higher than those of MAGI cells. For example, over 90% of Indicator #44 cells expressed all three receptors whereas less than 2% of MAGI, HUT78 and CEM-A cells expressed CCR5. Incubation of the cells with a control antimouse antibody, mouse IgG 2aκ-PE, yielded very low levels of non-specific binding of the antibody to the cells.

As shown in FIGS. 8A–G, the adenoviral vector-transduced HeLa cells significantly over-expressed all three HIV-1 receptors on the cells surface at very high levels. The level of expression and the number of cell expressing HIV-1 receptors can be regulated by controlling the m.o.i. of adenoviral vector to the cell number in this system. In comparison, the endogenous HUT-78 CD4 and CXCR4 expression was found to be at much lower levels than those observed in the HeLa cells transduced with rAd-R5-X4-D4-X4 vector (FIG. 8G).

The results indicate that the HeLa indicator cells transduced with the recombinant adenoviral vector of the present invention significantly over-expressed all three HIV-1 receptors (CD4, CXCR4, and CCR5) on the surface of the cells at a very high level. The values provided are representative of FACS data obtained with cells that have been transduced by the adenovirus vector at a multiplicity of infection (m.o.i.) of 20. The expression levels can be increased to 90–100% expression by raising the m.o.i. of the adenovirus vector to 25 or 30 in this system. Therefore, the percentage of cells expressing the HIV-1 receptors can be modulated and optimized to provide for the best level of sensitivity and concurrent lack of adenovirus vector toxicity for the cells.

7. Detection of Viral Infection of Indicator Cells by Various HIV Subtypes and Neutralization of HIV Infection by HIV-1 Antiserum Recombinant HeLa cells transduced by rAd-R5-X4-D4-X4 vector were tested for their ability to be infected by a wide variety of HIV subtypes in both laboratory and clinical isolates. In addition, an HIV-1 gp120 antiserum was tested using these cells for its ability to neutralize infection of HIV of various subtypes.

The HIV-1 primary isolates used in these assays were obtained from the National Institutes of Health AIDS Research and Reagent Reference Program (NIH-ARRRP), including HTLV-IIIB (Cat.#398, B/B clade), 92UG029 (Cat.#1650, A/A clade), 93RW002 (Cat.#1996, /A clade), 94UG103 (Cat.#2304, /A clade), 92TH014 (Cat.#1658, B/B clade), 93BR012 (Cat.#2308, /B clade, 92BR025 (Cat.#1777, C/C clade), 98CN006 (Cat.#4164, C/C clade), 92UG005 (Cat.#1684, D/D clade), 93UG065 (Cat.#1952, D/D clade), 93TH053 (Cat.#2166, /E clade), 93TH054 (Cat.#2167, /E clade), 93BR019 (Cat.#2314, /BF clade), 93BR020 (Cat.#2329, /F clade), 93BR029 (Cat.#2338, B/F clade), BCF13 (/O clade). HIV-1 gp120 antiserum (Cat. #385, lot #94002) was also obtained from the NIH-ARRRP.

The assays were performed in 96-well flat-bottom plates. The indicator cells ($3\times10^3$ cells) were mixed with rAd-R5-X4-D4-X4 vector at m.o.i. of 20 to 30. The HIV-1 strains from each subtype (clades A, B, C, D, E, F, and O) were prepared in duplicate wells. The amount of antibody and the number of cells were fixed at 4 μl antibody to $3\times10^3$ cells per well. The HIV-1 subtype virus inocula were adjusted to contain 50 to 600 infectious particle (i.p.) per well. After incubation of antibody with virus for about 10 hours, the virus and antibody mixtures were removed and replaced with the DMEM medium +10% CCS +antibiotics. HIV-1 infection can be observed after 24 to 48 hours by monitoring GFP expression as shown in Fig. X. At day 4, the culture medium was removed. The cells were washed with PBS once and 100 μl of PBS was added per well. The intensity of GFP expression was measured by a fluorescent microplate reader. The inhibitory concentrations of antibodies were calculated depending on the GFP fluorescent readings.

FIGS. 9A and 9B show the indicator cells in the absence and presence of HIV, respectively. As shown in FIG. 9A, in the absence of HIV, the HeLa cells containing a GFP reporter gene under the control of a molecular switch and transduced with rAd-R5-X4-D4-X4 vector show little expression of GFP. These cells are designated as "Indicator #44" cells. In contrast, in the presence of HIV-1/HTLV-IIIB (225 infectious particles), the viral infection of the cells turned on expression of the GFP reporter gene. As shown in FIG. 9B, there was a high level of GFP expression as indicated by the bright green fluorescence emitted by the GFP. It is noted that there was syncytia formed in the infected culture.

The anti-gp120 antiserum was tested for neutralizing HIV infection in the indicator cells. Indicator #44 cells were infected with 4000 infectious particles of HIV-1/HTLV-IIIB in the presence of anti-gp120 antiserum. As shown in FIG. 9C, antibodies containing in the anti-gp120 antiserum effectively neutralized the infection of HIV-1/HTLV-IIIB, as indicated by very low level of GFP expression. It was estimated that the anti-gp120 antiserum blocked about 83% of HIV infection.

Table 1 shown in FIG. 10 summarizes the results of the tests of susceptibility of the inventive indicator cells to infection of various HIV subtypes (or clades) and the ability of an anti-gp120 antiserum to neutralize infection these subtypes (or clades) of HIV in the indicator cells. In Table 1, X4 stands for CXCR4, and R5 for CCR5; SI stands for syncytia induction and NSI for no syncytia induction observed in the cells. As shown in Table 1, the indicator cells of the present invention is susceptible to HIV infection, regardless of HIV subtypes or coreceptor preference.

As also shown in Table 1, neutralizing antibodies made against HIV-1/HTLV-IIIB inhibited the replication of the HTLV-IIIB virus in these indicator cells by approximately 88%, whereas clade A virus was inhibited only 16% and clade C virus was inhibited only 8% by this specific antiserum at comparable virus levels.

Further, the indicator cells of the present invention are much more sensitive to infection of clinical isolates of HIV than indicators cells developed by others, such as MEGI cells. A table shown in FIG. 11 compares the i.p. per ml of cultures of these cells infected by a laboratory-adapted strain (HTLV-IIIB) of HIV and HIV patient isolates obtained from the NIH and Genphar, Inc. As shown in FIG. 11, the concentration of infectious particles of HIV from clinical isolates in the culture of HeLa cells transduced with rAd-R5-X4-D4-X4 vector (Indicator #44) is significantly higher than that in MEGI cell cultures. More dramatically, MEGI cells were completely incapable of being infected by a strain of HIV (93TH054) from a patient isolate. In stuck contrast to what was determined for MEGI cells, the concentration of i.p. in Indicator #44 cell culture reached a high level of 4,800 i.p./ml.

Figure 12:
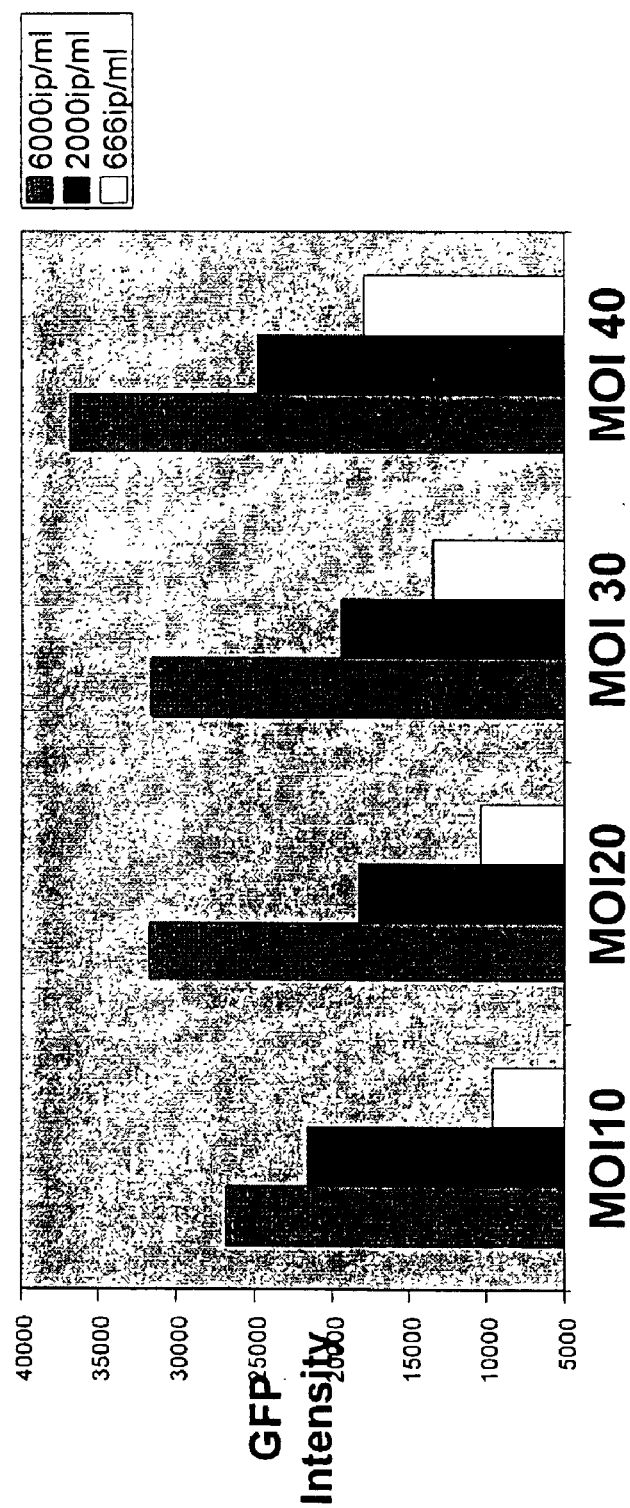
FIG. 12 shows intensities of GFP expressed by HeLa cells transduced with rAd-R5-X4-D4-X4 (Indicator #44 cells) at various m.o.i. and infected by HIV at various i.p. concentrations.

The present invention also demonstrates that the ability of HIV to infect and replicate in the indicator cell culture correlates with the levels of HIV receptors expressed by the indicator cells. indicator #44 cell culture transduced with the recombinant adenoviral vector, rAd-R5-X4-D4-X4, at various m.o.i. (10, 20, 30, and 40) were infected by a laboratory-adapted strain of HIV (HIV-1/HTLV-IIIB) at different i.p. concentrations (666, 2000, and 6000 i.p./ml). Intensity of GFP expressed by the indicator #44 cells was measured. This study was conducted in duplicate and the GFP intensities from the two studies were averaged. FIG. 12 is a graph showing the averaged intensities of GFP expressed from the indicator cells transduced with rAd-R5-X4-D4-X4 at 10–40 m.o.i. and infected by HTLV-IIIB at 666–6000 i.p./ml concentrations.

As shown in FIG. 12, the higher the m.o.i. of the recombinant adenoviral vector is, the higher GFP intensity is.

These results indicate that the higher levels of HIV receptors expressed from the cells, the more susceptible the cells are to HIV infection.

These data suggest that recombinant cells of the present invention can be used as a sensitive assay for detecting HIV infection and as a neutralization assay for laboratory and clinical sub-types found worldwide. The neutralization assay can be used to determine the broad-spectrum neutralizing antibody responses of candidate HIV-1 vaccines both in immunized animals and humans.

8. Neutralization of HIV Infection by HIV-1 Antiserum from Animals Immunized with Recombinant Adenoviral Vaccines The neutralization assay is used for measuring neutralizing antibody levels in sera from mice immunized with the recombinant adenoviral vector (rAd) vaccines described in Section 5. As shown above, the inventive HIV-1 indicator cells were able to detect and measure the neutralization of HIV-1 isolates and viruses from the various clades using an HIV-1 IIIB antiserum. Mice (4 mice for each group) are immunized with the single-clade and multi-clade HIV-1 env vaccines and the humoral immune responses against the HIV antigens are measured by ELISAs and neutralizing antibodies are measured with the neutralization assay described above. Two series of immunizations are carried out. For both series, C57BL/6 mice are inoculated intramuscularly with $10^7$ pfu of rAd vector vaccine. "Series 1" mice are reinoculated with an additional $10^7$ pfu of vaccine at 10 weeks subsequent to the primary inoculation. "Series 2" mice are re-inoculated eight weeks after the primary inoculation. Blood is collected at two-week intervals following the primary and secondary inoculations. Serum antibodies specific for HIV proteins are detected by ELISA using cell lysates that contain HIV proteins or purified recombinant proteins as antigens. Mice inoculated with the rAd env vaccines should produce clade-specific antibodies against HIV-1 env proteins. The neutralizing activity and cross-reactivity of the mouse antisera produced are determined using the neutralization assay of the present invention.

The neutralization assay is also used for measuring neutralizing antibody levels in sera from humans immunized with vaccines or candidate vaccines under clinical trials. The neutralizing antibodies elicited by the vaccines are purified from patient serum, considering that measurement of patients' neutralizing antibody activities may be influenced by these two factors: (1) the presence of residual anti-HIV drug in the patient's serum might inhibit virus infection and (2) HIV-1 infectious virus already present in the patient's serum might decrease the level of neutralizing antibodies detected in the assay.

Protein A and Protein G agarose is used for purification of antibodies from patient serum (Roche, 1134515 for Protein A; 1719416 for Protein G). The purified patient antibodies are mixed with clade-specific HIV-1 virus and applied to the HIV-1 indicator cells of the present invention for neutralization assays as described above.

Based on the data obtained from the neutralization assays, a panel of HIV-1 isolates of different co-receptor preferences and from different clades and geographic regions of the world is compiled for testing the broad neutralizing activities of the sera from immunized individuals receiving candidate AIDS vaccines. Clinical isolates of different co-receptor preferences and clades are obtained from a number of sources such as the NIH-ARRRP. Selected isolates are propagated, grouped into panels, and used for testing the broad neutralizing activities of the sera from immunized individuals receiving candidate HIV-1 vaccines.

In addition, standardized virus panels can be obtained from the NIAID DAIDS Program and from international sources for direct comparisons of the neutralization profiles of antibodies elicited by candidate multi-clade and multi-isolate vaccines in experimental animals and in clinical samples from ongoing candidate vaccine trials.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A method for screening a tester agent for anti-HIV activity, comprising:

taking a culture of recombinant cells in which at least one of the recombinant cells comprises a reporter sequence comprising a reporter gene whose expression is regulated by a protein specific to HIV, and the recombinant cell is genetically modified to express two or more cell surface receptors for HIV, each at an elevated level relative to the level of the corresponding cell surface receptor for HIV naturally expressed in a human cell, such that productive infection of the recombinant cell by HIV is achieved, which is defined by HIV viral replication and the infection of non-infected cells in the culture of the recombinant cells;

contacting the cell culture with a sample containing HIV;

adding a tester agent to the cell culture; and detecting a change in a level of expression of the reporter gene in the cells in the culture.

2. The method according to claim 1, wherein the reporter gene expression is up-regulated by the HIV specific protein.

3. The method according to claim 1, wherein the HIV specific protein is an HIV transactivator protein.

4. The method according to claim 3, wherein the HIV trans activator protein is Tat.

5. The method according to claim 1, wherein the reporter sequence comprises a promoter, an HIV-specific enhancer sequence, and a reporter gene whose expression is regulated by binding of an HIV-specific transactivator protein to the HIV specific enhancer sequence.

6. The method according to claim 5, wherein the HIV specific transactivator protein is Tat and the HIV-specific enhancer sequence comprises at least one copy of TAR sequence.

7. The method according to claim 6, wherein the HIV-specific enhancer comprises at least two copies of TAR sequence.

8. The method according to claim 1, wherein the reporter gene is selected from the group consisting of genes encoding b-galactosidase, luciferase, b-glucuronidase, chloramphenicol acetyl transferase (CAT), secreted embryonic alkaline phosphatase (SEAP), hormones, cytokines and green fluorescent protein (GFP).

9. The method according to claim 1, wherein the two or more cell surface receptors for HIV expressed by the recombinant cell are selected from the group consisting of CD4, CXCR4, CCR5, CCR1, CGR2b, CCR3, CCR4, CCR8, CXCR1, CXCR2, CXCR3, CX₃CR1, STRL33/BONZO and GPR15/BOB.

10. The method according to claim 1, wherein the two or more cell surface receptors for HIV expressed by the recombinant cell comprises CD4 and CXCR4.

11. The method according to claim 1, wherein the two or more cell surface receptors for HIV expressed by the recombinant cell comprises CD4 and CCR5.

12. The method according to claim 1, wherein the two or more cell surface receptors for HIV expressed by the recombinant cell comprises CD4, CXCR4 and COR5.

13. The method according to claim 1, wherein the recombinant cell expresses a sufficient number of cell surface receptors to render the recombinant cell susceptible to infection of substantially all strains of HIV.

14. The method according to claim 1, wherein the recombinant cell expresses a sufficient number of cell surface receptors to render the recombinant cell susceptible to infection of substantially all subtypes or clades of HIV.

15. The method according to claim 1, wherein the recombinant cell expresses a sufficient number of cell surface receptors to render the recombinant cell susceptible to infection of clinical isolates of HIV.

16. The method according to claim 1, wherein the recombinant cell is a tumor cell.

17. The method according to claim 1, wherein the recombinant cell is a cell which has been immortalized by introducing a gene into the cell which renders the cell immortalized.

18. The method according to claim 1, wherein the recombinant cell is capable of achieving productive infection of a clinically isolated HIV.

19. The method according to claim 1, wherein the two or more cell surface receptors for HIV include CD4 and are expressed by an adenoviral vector transduced into the recombinant cell.

20. The method according to claim 19, wherein the adenoviral vector is replication incompetent.

21. The method according to claim 19, wherein the adenoviral vector has 1–100 multiplicity of infection.

22. The method according to claim 19, wherein the adenoviral vector has 10–60 multiplicity of infection.

23. The method according to claim 19, wherein CD4 is expressed from the E1 region of the adenoviral vector while the one or more additional cell surface receptors are expressed from E3 or E4 region of the adenoviral vector.

24. The method according to claim 19, wherein the one or more additional cell surface receptors are expressed from the E1 region of the adenoviral vector while CD4 is expressed from E3 or E4 region of the adenoviral vector.

25. The method according to claim 19, wherein the cell surface receptors for HIV include CCR5 and CXCR4 that are bicistronically expressed from E1, E3, or E4 region of the adenoviral vector by a splicing mechanism or via an internal ribosome entry site.

26. The method according to claim 19, wherein CD4 and the one or more additional cell surface receptors are bicistronically expressed from E1, E3, or E4 region of the adenoviral vector by a splicing mechanism or via an internal ribosome entry site.

27. The method according to claim 19, wherein the cell surface receptors for HIV include CCR5 and CXCR4 that are bicistronically expressed from E1 region of the adenoviral vector while CXCR4 and CD4 are bicistronically expressed from E4 region of the adenoviral vector.

28. The method according to claim 19, wherein the E1 region of the adenoviral vector retains native E1 promoter of the adenoviral vector.

29. The method according to claim 19, wherein the native E1 promoter of the adenoviral vector is replaced by an exogenous promoter for expressing CD4 or the one or more additional cell surface receptors.

30. The method according to claim 29, wherein the exogenous promoter is a CMV promoter.

31. The method according to claim 19, wherein the adenoviral vector includes an adenoviral packaging signal.

32. The method according to claim 19, wherein the adenoviral vector includes a eukaryotic polydenylation sequence.

33. The method according to claim 32, wherein the eukaryotic polyadenylation sequence is a bovine growth hormone or SV40 polyadenylation site.

34. The method according to claim 1, wherein the tester agent is added to the cell culture before the cell culture is contacted with the HIV.

35. The method according to claim 1, wherein the tester agent is added to the cell culture after the cell culture is contacted with the HIV.

36. The method according to claim 1, wherein the tester agent and the HIV are added to the cell culture simultaneously.

37. The method according to claim 1, wherein the tester agent is a natural product or synthetic composition.

38. The method according to claim 1, wherein the tester agent is isolated from body fluid or tissues of a human or non-human animal.

39. The method according to claim 1, wherein the tester agent is selected from the group consisting of whole blood, blood serum, isolated peripheral blood cells, T cells, spleens, and bone marrow.

40. The method according to claim 1, wherein the tester agent is a polyclonal or monoclonal antibody.

41. The method according to claim 40, wherein the antibody is a fully assembled antibody, a Fab fragment, or a single chain antibody.

42. The method according to claim 1, wherein the tester agent is an inhibitor of viral reverse transcriptase, protease, or integrase.

43. The method according to claim 1, wherein the tester agent is a protein or peptide that binds to HIV Env, TAR, or RRE.

44. The method according to claim 1, wherein the tester agent is a protein or peptide that binds to CD4 or an HIV coreceptor.

45. The method according to claim 1, wherein the tester agent is blood serum isolated from an animal immunized with an HIV vaccine.

46. The method according to claim 1, wherein the tester agent is an antibody or a combination of antibodies isolated from blood serum of an animal immunized with an HIV vaccine.

47. The method according to claim 1, wherein the tester agent is blood serum isolated from an individual immunized with an HIV vaccine or a candidate vaccine under a clinical trial.

48. The method according to claim 1, wherein the tester agent is an antibody or a combination of antibodies isolated from blood serum of an individual immunized with an HIV vaccine or a candidate vaccine under a clinical trial.

49. The method according to claim 45, wherein the vaccine is a vaccine against a HIV-1 clade selected from the group consisting of clade A, B, C, D, E, F, and O.

50. The method according to claim 45, wherein the vaccine is a vaccine against at least two HIV-1 clades selected from the group consisting of clade A, B, C, D, E, F, and O.

51. The method according to claim 45, wherein the vaccine is an adenoviral vector vaccine encoding an antigen from an HIV-1 clades selected from the group consisting of clade A, B, C, D, E, F, and O.

52. The method according to claim 45, wherein the vaccine is an adenoviral vector vaccine encoding two antigens from two different HIV-1 clades selected from the group consisting of clade A, B, C, D, E, F, and O.

53. The method according to claim 1, wherein the HIV contained in the sample is HIV-1 clade A, B, C, D, E, F, or O.

54. The method according to claim 1, wherein the HIV contained in the sample is a laboratory isolate of HIV-1.

55. The method according to claim 1, wherein the HIV contained in the sample is a clinical isolate of HIV-1.

56. The method according to claim 1, wherein the sample containing HIV is a blood sample of an individual infected with HIV.

57. The method according to claim 1, wherein the sample containing HIV is a blood sample of an individual infected with HIV and being treated with an anti-HIV drug.

58. The method according to claim 29, wherein the exogenous promoter is selected from a basic promoter region of a promoter selected from the group consisting of b-actin promoter, insulin promoter, human cytomegalovirus promoter, Rous sarcoma virus promoter, and simian virus SV40 promoter.

59. The method of claim 19, wherein the adenoviral vector further comprises a gene encoding an interleukin that renders the transduced cells more susceptible to HIV infection.

60. The method of claim 59, wherein the gene encoding an interleukin is a wild-type or recombinant gene encoding interleukin-2 or interleukin-12.

61. A method for detecting HIV drug resistance in a sample, comprising:
taking a cell culture of recombinant cells in which at least one of the recombinant cells comprises a reporter sequence comprising a reporter gene whose expression is regulated by a protein specific to HIV, and the recombinant cell is genetically modified to express two or more cell surface receptors for HIV, each at an elevated level relative to the level of the corresponding cell surface receptor for HIV naturally expressed in a human cell, such that productive infection of the recombinant cell by the HIV virus is achieved, which is defined by HIV viral replication and the infection of non-infected cells in a culture of the recombinant cells;
contacting the cell culture with a sample containing HIV;
adding one or more anti-HIV agents to the cell culture either before or after contacting the cell culture with the sample; and
detecting a change in a level of expression of the reporter gene in the cells.

62. The method according to claim 61, wherein the reporter gene is selected from the group consisting of genes encoding b-galactosidase, luciferase, b-glucuronidase, chloramphenicol acetyl transferase (CAT), secreted embryonic alkaline phosphatase (SEAP), hormones, cytokines and green fluorescent protein (GFP).

63. The method according to claim 61, wherein the two or more cell surface receptors for HIV are selected from the group consisting of CD4, CXCR4, CCR5, CCR1, CCR2b, CCR3, CCR4, CCR8, CXCR1, CXCR2, CXCR3, CX$_3$CR1, STRL33/BONZO and GPR15/BOB.

64. The method according to claim 61, wherein the two or more cell surface receptors for HIV are CD4, CXCR4 and CCR5.

65. The method according to claim 61, wherein the sample containing HIV is a clinical isolate of HIV.

66. The method according to claim 61 wherein the sample containing HIV is blood isolated from an HIV-infected individual.

67. The method according to claim 61, wherein the sample containing HIV is plasma isolated from an HIV-infected individual.

* * * * *